(12) United States Patent
Kurata et al.

(10) Patent No.: US 10,234,414 B2
(45) Date of Patent: Mar. 19, 2019

(54) MEASUREMENT APPARATUS, AND METHOD FOR OPERATING MEASUREMENT APPARATUS

(71) Applicant: ARKRAY, Inc., Kyoto (JP)

(72) Inventors: Yuji Kurata, Kyoto (JP); Kazuo Fukuda, Kyoto (JP); Yoshiharu Sato, Kyoto (JP); Gai Go, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 388 days.

(21) Appl. No.: 14/710,496

(22) Filed: May 12, 2015

(65) Prior Publication Data
US 2016/0018353 A1   Jan. 21, 2016

(30) Foreign Application Priority Data

May 13, 2014 (JP) .................. 2014-099804
May 13, 2014 (JP) .................. 2014-099805
May 13, 2014 (JP) .................. 2014-099806
Apr. 16, 2015 (JP) .................. 2015-084244

(51) Int. Cl.
*G01N 27/327* (2006.01)
*G01N 33/487* (2006.01)

(52) U.S. Cl.
CPC ... *G01N 27/3273* (2013.01); *G01N 33/48764* (2013.01); *G01N 27/3272* (2013.01)

(58) Field of Classification Search
CPC ........... G01N 27/3273; G01N 27/3272; G01N 33/48764
See application file for complete search history.

(56) References Cited

U.S. PATENT DOCUMENTS

| | | | |
|---|---|---|---|
| 4,509,859 A | 4/1985 | Markart et al. | |
| 5,395,504 A | 3/1995 | Saurer et al. | |
| 5,707,197 A | 1/1998 | Jaeger | |
| 6,151,110 A | 11/2000 | Markart | |
| 2003/0211619 A1* | 11/2003 | Olson ................ | A61B 5/15146 436/44 |
| 2005/0145491 A1 | 7/2005 | Amano et al. | |

(Continued)

FOREIGN PATENT DOCUMENTS

| | | |
|---|---|---|
| CA | 2132379 A1 | 3/1995 |
| EP | 2315012 A2 | 4/2011 |

(Continued)

OTHER PUBLICATIONS

The extended European search report issued by the European Patent Office dated Sep. 25, 2015, which corresponds to European Patent Application No. 15167668.1-1554 and is related to U.S. Appl. No. 14/710,496.

(Continued)

*Primary Examiner* — J. Christopher Ball
(74) *Attorney, Agent, or Firm* — Studebaker & Brackett PC

(57) ABSTRACT

A measurement apparatus to measure a physical quantity related to a measurement target by use of a sensor, comprising: an apparatus enclosure; a control unit to be electrically connected to the sensor; and a moving member including a sensor holding unit to hold the sensor, the moving member being movable to protrude the sensor holding unit outwardly of the apparatus enclosure and further including a conductive member to electrically connect the sensor to the control unit.

17 Claims, 24 Drawing Sheets

(56) References Cited

U.S. PATENT DOCUMENTS

| | | |
|---|---|---|
| 2005/0230253 A1 | 10/2005 | Marquant |
| 2008/0021296 A1 | 1/2008 | Creaven |
| 2008/0131322 A1 | 6/2008 | Kheiri et al. |
| 2008/0286149 A1 | 11/2008 | Roe et al. |
| 2009/0149725 A1 | 6/2009 | Gofman et al. |
| 2010/0096403 A1 | 4/2010 | Amano et al. |
| 2011/0094881 A1 | 4/2011 | Watanabe |
| 2012/0171757 A1 | 7/2012 | Kheiri et al. |
| 2012/0282138 A1 | 11/2012 | Gofman et al. |
| 2013/0050446 A1 | 2/2013 | Matsuoka |
| 2014/0079607 A1 | 3/2014 | Kheiri et al. |
| 2014/0241958 A1 | 8/2014 | Kheiri et al. |

FOREIGN PATENT DOCUMENTS

| | | |
|---|---|---|
| GB | 2096314 A | 10/1982 |
| JP | 07-151721 A | 6/1995 |
| JP | 2004-004046 A | 1/2004 |
| JP | 3954393 B2 | 8/2007 |
| JP | 2008-504532 A | 2/2008 |
| JP | 2008-518204 A | 5/2008 |
| JP | 4221372 B2 | 2/2009 |
| JP | 2011-508872 A | 3/2011 |
| JP | 2012-202716 A | 10/2012 |
| JP | 5095850 B1 | 12/2012 |

OTHER PUBLICATIONS

An Office Action issued by the Japanese Patent Office dated Oct. 17, 2017, which corresponds to Japanese Patent Application No. 2014-099804 and is related to U.S. Appl. No. 14/710,496.

An Office Action issued by the Japanese Patent Office dated Dec. 18, 2018, which corresponds to Japanese Patent Application No. 2015-084244 and is related to U.S. Appl. No. 14/710,496; with English translation.

* cited by examiner

MEASUREMENT APPARATUS, AND METHOD FOR OPERATING MEASUREMENT APPARATUS

CROSS-REFERENCE TO RELATED APPLICATION

This application is based upon and claims the benefit of priority of the prior Japanese Patent Applications No. 2014-099804 filed on May 13, 2014, No. 2014-099805 filed on May 13, 2014, No. 2014-099806 filed on May 13, 2014 and No. 2015-084244 filed on Apr. 16, 2015, the entire contents of which are incorporated herein by reference.

TECHNICAL FIELD

The present invention relates to a measurement apparatus to measure a physical quantity, and a method for operating a measurement apparatus.

BACKGROUND ART

A measurement apparatus (refer to, e.g., Patent Documents 1 and 2) called a blood glucose self-measurement apparatus is known as an apparatus capable of measuring a blood glucose level in home and at a workplace, the apparatus being used by setting a sensor cartridge containing a plurality of disposal sensors for measuring the blood glucose level.

These measurement apparatuses can be roughly classified into a measurement apparatus used by setting a sensor whenever measuring the blood glucose level (which will hereinafter be termed a non sensor built-in type apparatus), and a measurement apparatus housing a plurality of sensors inside, one intra-apparatus sensor moving to a measurement position upon performing a predetermined operation when measuring (which will hereinafter be termed a sensor built-in type apparatus).

The non sensor built-in type apparatus generally uses the sensor taking a rectangular shape and provided with an electrode at one end in a longitudinal direction thereof (which will hereinafter be referred to as a tail end) and with a blood introduction port at the other end (which will hereinafter be referred to as a leading end). An apparatus enclosure of the non sensor built-in type apparatus is formed with a sensor insertion port for inserting the sensor. The non sensor built-in type apparatus is configured so that the leading end of the sensor comes to a state of protruding approximately 2 cm from the apparatus enclosure upon inserting the tail end of the sensor into the sensor insertion port and securing the sensor in order to facilitate an operation of bringing the blood into contact with a blood introduction port (which will hereinafter be termed a droplet applying operation).

The general sensor built-in type apparatus is configured so that the leading end of the sensor taken out from a sensor housing unit (which is normally a sensor cartridge) within the apparatus protrudes approximately 1-2 cm from the apparatus enclosure in order to facilitate the droplet applying operation.

Known also is the sensor built-in type apparatus (e.g., Patent Document 3) using a removable multi-region sensor taking such a shape that a plurality of sensors is strung together. However, this sensor built-in type apparatus is also configured so that a part (one sensor) of the removable multi-region sensor protrudes from the apparatus enclosure.

The sensor housed in the sensor cartridge for the measurement apparatus is deteriorated due to a water content (humidity) as the case may be. It is therefore proposed that a desiccant is put into the sensor cartridge, and the sensor cartridge or the measurement apparatus incorporates a hermetic closing mechanism for hermetically closing the sensor cartridge when not using the measurement apparatus (refer to, e.g., Patent documents 4-6).

DOCUMENTS OF PRIOR ARTS

Patent Documents

[Patent Document 1] Japanese Patent Application Publication No. 4221372
[Patent Document 2] Japanese Unexamined Patent Application Publication No. 2011-508872
[Patent Document 3] Japanese Patent Application Publication No. H07-151721
[Patent Document 4] Japanese Patent Application Publication No. 3954393
[Patent Document 5] Japanese Unexamined Patent Application Publication No. 2008-504532
[Patent Document 6] Japanese Patent Application Publication No. 5095850

SUMMARY

The existing measurement apparatus described above adopts a configuration that is substantially complicated as the configuration for taking out the sensor from the sensor cartridge and causing the sensor to protrude outwardly of the enclosure of the measurement apparatus. The existing measurement apparatus consequently leads to an increase in manufacturing cost.

It is preferable in terms of reducing the sensor manufacturing cost and a sales price to downsize the sensor of the measurement apparatus (the sensor built-in type apparatus or the non sensor built-in type apparatus) described above. However, the sensor being downsized, the blood introduction port of the sensor becomes proximal to the apparatus enclosure, and hence the droplet applying operation is hard to perform when making the measurement.

A problem that the droplet applying operation becomes difficult due to the downsizing of the sensor, can occur in the measurement apparatus using the disposal sensor (e.g., the measurement apparatus measures temperatures of wastewater, pollutant and other equivalent measurement targets by using the disposal sensor).

Every existing hermetic closing mechanism has the substantially complicated configuration. The incorporation of the hermetic closing mechanism having the complicated configuration into the sensor cartridge or the measurement apparatus results in increasing the costs for manufacturing the sensor cartridge and the measurement apparatus.

Under such circumstances, it is an object of the present invention to provide a technology capable of downsizing a sensor without causing any difficulty to perform a droplet applying operation.

To accomplish the object described above, a measurement apparatus to measure a physical quantity related to a measurement target by use of a sensor, includes: an apparatus enclosure; a control unit to be electrically connected to the sensor; and a moving member including a sensor holding unit to hold the sensor, the moving member being movable to protrude the sensor holding unit outwardly of the apparatus enclosure and further including a conductive member to electrically connect the sensor to the control unit.

To be specific, the measurement apparatus according to the present invention has a configuration that a portion to hold the sensor (the sensor holding unit) protrudes from the apparatus enclosure. Upon the protrusion of the portion to hold the sensor from the apparatus enclosure, the droplet applying operation can be easily performed even when the sensor is of a small size. The measurement apparatus according to the present invention can be said to be an apparatus not causing the difficulty to perform the droplet applying operation even when downsizing the sensor.

The measurement apparatus according to the present invention may be attained as the apparatus further including a flexible board to electrically connect the conductive member to the control unit. In the measurement apparatus according to the present invention, the "moving member" may be a member molded integrally with the conductive member.

The measurement apparatus according to the present invention may be attained as the apparatus configured so that "the sensor holding unit is housed in the apparatus enclosure when standing by", and may also be attained as the apparatus configured so that "the moving member includes a main slider and a sub-slider, and the sensor is pinched in between the main slider and the sub-slider and is thus held".

A measurement apparatus to measure a physical quantity related to a measurement target by use of a sensor according to the present invention includes: an apparatus enclosure; a housing unit to house a sensor cartridge containing a plurality of sensors; and a moving member to move for causing the sensor to protrude outwardly of the apparatus enclosure, and the moving member may have a hermetic closing unit to seal an aperture of the sensor cartridge.

To be specific, the measurement apparatus according to the present invention may have a configuration that the aperture of the sensor cartridge housed in the housing unit is sealed by the hermetic closing unit possessed by the moving member for causing the sensor within the sensor cartridge to protrude outwardly of the apparatus (enclosure). Such a configuration can be attained by a small number of components. According to the present invention, it is therefore feasible to attain inexpensively (manufacture) the measurement apparatus capable of hermetically closing the sensor cartridge when standing by.

With the foregoing configuration being adopted, it is possible to use the sensor cartridge not having any hermetic closing configuration/mechanism. It therefore follows that according to the present invention, the sensor cartridge as a consumable product can be provided to a user at a low cost.

It may be sufficient that the "hermetic closing unit according to the present invention can seal the aperture of the sensor cartridge. For example, for improving the hermetic closing property of the hermetic closing unit to seal the sensor cartridge, a flexural portion may be adopted as the "hermetic closing unit". With respect to the "hermetic closing unit", the apparatus enclosure may be provided with a pressing member to press the hermetic closing unit against the aperture of the sensor cartridge. The apparatus enclosure may also be provided with both of the pressing member and the flexural member. The "hermetic closing unit" including an elastic rubber may also be adopted.

The measurement apparatus to measure a physical quantity according to the present invention includes: an apparatus enclosure to house a sensor to which a droplet of measurement target having a physical quantity is applied; and a moving member to cause the sensor to protrude from the apparatus enclosure in a state of holding the sensor. The moving member of the measurement apparatus according to the present invention is configured to be enabled to advance and retreat between a first position with the sensor protruding from the apparatus enclosure, a second position with the sensor retreating from the first position, and a third position with the sensor appearing in a position to engage with the moving member advancing to the first position by moving from the second position.

To be specific, the measurement apparatus according to the present invention has a configuration that the sensor is taken out from within the apparatus enclosure and protruded outwardly of the apparatus enclosure by the moving member "configured to be enabled to advance and retreat between the first position with the sensor protruding from the apparatus enclosure, the second position with the sensor retreating from the first position, and the third position with the sensor appearing in the position to engage with the moving member advancing to the first position by moving from the second position". The moving member having such a function can be attained easily (by the small number of components). It is therefore feasible to inexpensively manufacture the measurement apparatus by adopting the configuration of the measurement apparatus according to the present invention.

Note that the first position in the measurement apparatus according to the present invention may be a position in which an end surface of the moving member protrudes from the apparatus enclosure, and may also be a position in which the end surface of the moving member does not protrude from the apparatus enclosure. The measurement apparatus, on the occasion of attaining the measurement apparatus according to the present invention, may adopt a configuration that "the moving member causes the sensor to appear in front of the tip of the moving member by retreating to the third position from the second position, and the tip of the moving member holds the sensor appearing in front thereof when advancing to the first position from the third position".

The measurement apparatus according to the present invention may have an addition of "a carrying mechanism to carry the sensor to the front of the tip in the third position in linkage with the retreat of the moving member to the third position".

For restraining the sensor within the apparatus enclosure from deteriorating due to a water content (humidity), the measurement apparatus according to the present invention may have additions of "a sensor housing unit to be provided within the apparatus enclosure and to have an outlet of the sensor; and an opening/closing member to close the outlet when the moving member is located at least in the second position and to open the outlet when the moving member is located at least in the third position".

The measurement apparatus according to the present invention may adopt a configuration that "the apparatus enclosure is provided with a protrude portion to keep the position of the moving member in the first position and a protruded portion to keep the position of the moving member in the second position, and the moving member includes an engaging portion to cause the moving member to engage with the apparatus enclosure in the first position or the second position by engaging with the protruded portion of the apparatus enclosure, the engaging portion becoming flexural upon applying force onto the moving member in the retreating direction and thereby moving over the protruded portion kept in engagement"

The measurement apparatus according to the present invention may have an addition of "a disengaging mechanism to disengage the sensor from the moving member when the moving member retreats to the second position from the first position", the disengaging mechanism including, e.g., "a movement inhibiting member to inhibit the sensor from moving together with the moving member by abutting on an edge, on the side of the moving member, of the sensor held by the moving member being on the movement toward the second position". Note that the addition of the disengaging mechanism enables the attainment of the measurement apparatus configured so that the sensor used for the measurement is automatically removed from the tip of the moving member when the moving member moves to the second position.

The moving member of the measurement apparatus according to the present invention may be one member or one assembly and may also be "the moving member including: a first slider to move the sensor being movable between the first position and the third position to such a position as to abut on a tip of the first slider when moving to the third position from the second position, the sensor having moved to the abutting position engaging with the tip of the first slider when moving to the first position; and a second slider to pinch the sensor between a tip of the second slider and the tip of the first slider by fitting to the first slider after the sensor has engaged with the tip of the first slider being on the movement toward the first position".

The measurement apparatus according to the present invention may also have an addition of "a carrying mechanism to carry the sensor to the front of the tip of the slider in the third position in linkage with the retreating of the slider to the third position".

The measurement apparatus according to the present invention has the addition of "the disengaging mechanism to disengage the sensor held by the tip when the slider retreats to the second position from the first position". This addition results in attaining the measurement apparatus configured to automatically remove the sensor used for the measurement from the tip of the slider when the slider moves to the standby position. Note that the disengaging mechanism can adopt a variety of different specific configurations. For example, it is feasible to adopt the disengaging mechanism including "the movement inhibiting member to inhibit the sensor from moving together with the moving member by abutting on the edge, on the side of the moving member, of the sensor held by the tip of the moving member being on the movement toward the second position".

The measurement apparatus according to the present invention may also adopt a configuration that "the sensor is a sensor housed in the sensor cartridge set in the apparatus enclosure, the sensor cartridge including:
a reel to be wound with a sensor element having a plurality of sensors bonded one by one onto one surface of a tape-shaped mount film along a longitudinal direction of the mount film, the sensor having an end portion being exfoliated from the mount film when bending a portion with existence of the end portion of a certain sensor at a curvature equal to or smaller than a predetermined curvature in the longitudinal direction so that one surface side of the sensor is convexed;
a case to have a sensor protruding port and to house the reel therein, the sensor element being disposed in the case so that the sensor element unwound from the reel passes through the sensor protruding port and is bent toward the film housing port to exfoliate a part of the sensor from the mount film of the sensor element; and
a rotary body to be housed in the case and enabled to rotate from outside the case, the rotary body moving the sensor element within the case in an unwinding direction of the sensor element wound on the reel by the rotary body rotating in a predetermined direction from outside the case,
the measurement apparatus further comprising a drive mechanism to rotate the rotary body of the sensor cartridge housed in the housing unit in the predetermined direction so that a next sensor protrudes from the sensor protruding port of the case by converting a part of rectilinear motion of the moving member toward the third position into a rotary motion".

Further, a method for operating a measurement apparatus according to the present invention is a method for operating a measurement apparatus including an apparatus enclosure to house a sensor to which a droplet of measurement target having a physical quantity is applied; and a moving member to protrude the sensor from the apparatus enclosure in a state of holding the sensor, the method including:
a step of causing the sensor to appear in such a position that the moving member engages with the sensor by retreating the moving member to a third position from a second position as a standby position;
a step of protruding the sensor from the apparatus enclosure by advancing the moving member to a first position in front of the second position from the third position to engage with the sensor; and
a step of retreating the moving member to the second position from the first position after applying the droplet of measurement target to the sensor protruded from the apparatus enclosure.

The method for operating the measurement apparatus according to the present invention may be carried out so that "the step of causing the sensor to appear includes causing the sensor to appear in front of a tip of the moving member, and the step of protruding the sensor includes causing the tip of the moving member to engage with the sensor appearing in front of the tip thereof".

According to the present invention, the sensor can be downsized without causing any difficulty to perform the droplet applying operation.

DESCRIPTION OF EMBODIMENTS

First Embodiment

Figure 1:
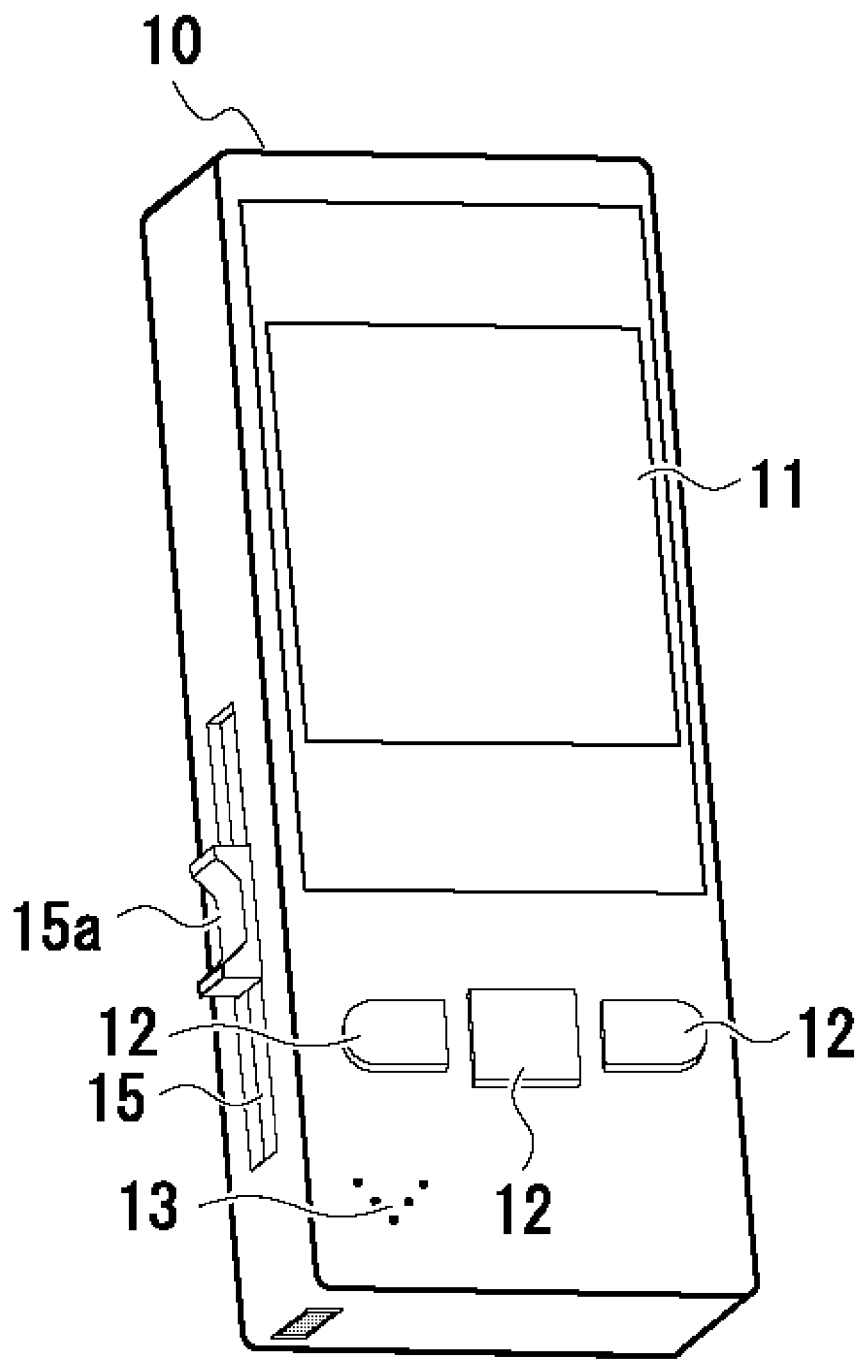
FIG. 1 is a diagram of an external appearance of a measurement apparatus according to a first embodiment of the present invention.

FIG. 1 illustrates an external appearance of a measurement apparatus according to a first embodiment of the present invention.

The measurement apparatus according to the first embodiment is a blood glucose level measurement apparatus that is used by setting a sensor cartridge therein. As illustrated in FIG. 1, the measurement apparatus includes an apparatus enclosure 10, an LCD (Liquid Crystal Display) 11, three push button switches 12 and a speaker 13, these components 11, 12, 13 being disposed on a front surface (the surface on the near side in FIG. 1) of the apparatus enclosure 10. The measurement apparatus further includes slider 15 sliding vertically together with a slider knob 15a by operating the slider knob 15a disposed on a side surface of the apparatus enclosure 10.

Figure 3:
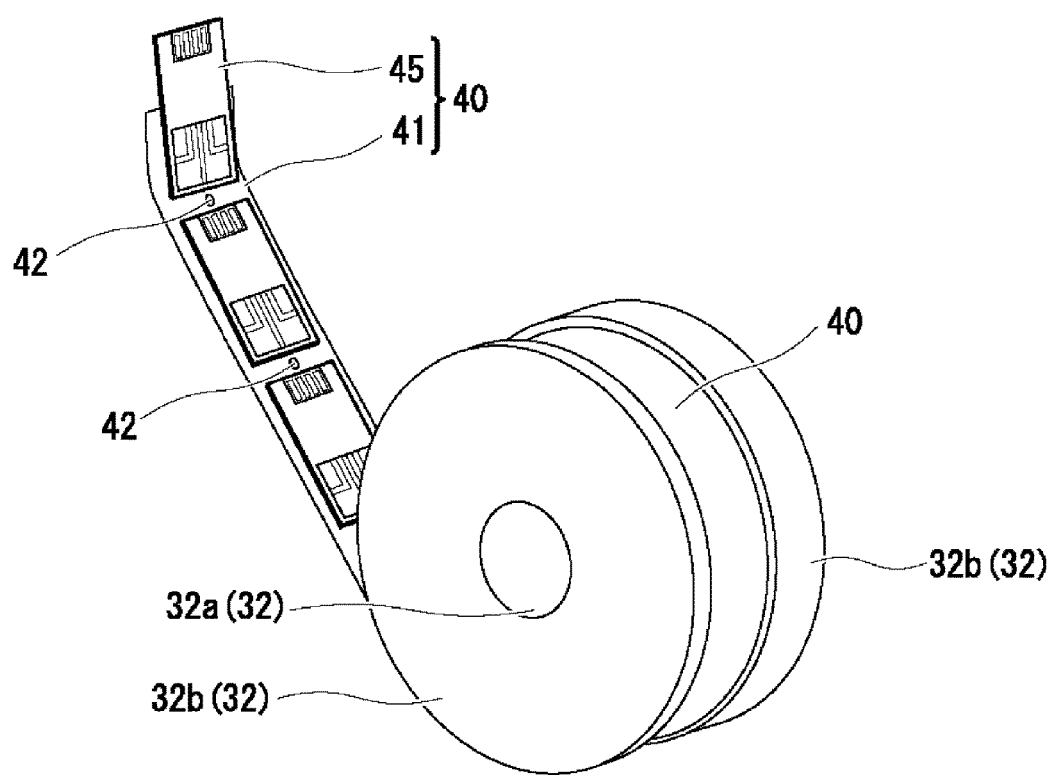
FIG. 3 is a view of an external appearance of a reel hub wound with a sensor element, the hub being housed in the sensor cartridge.
Figure 4A:
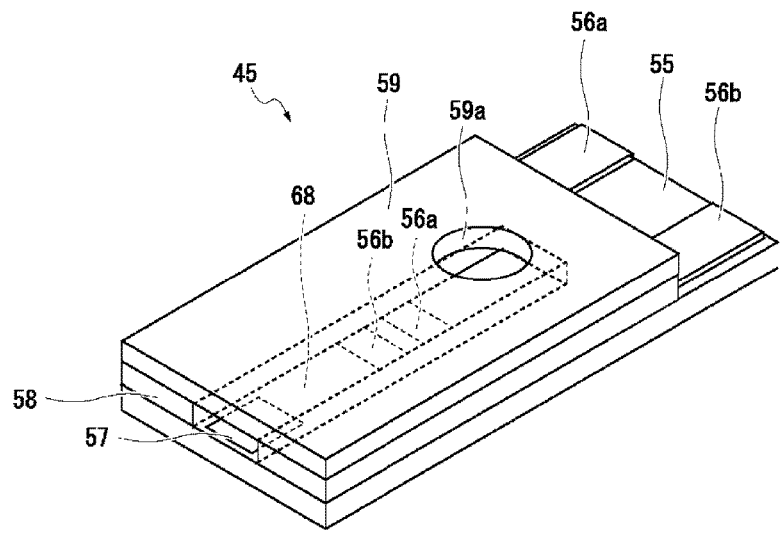
FIG. 4A is an explanatory view of an example of a configuration of a film-shaped sensor.
Figure 4B:
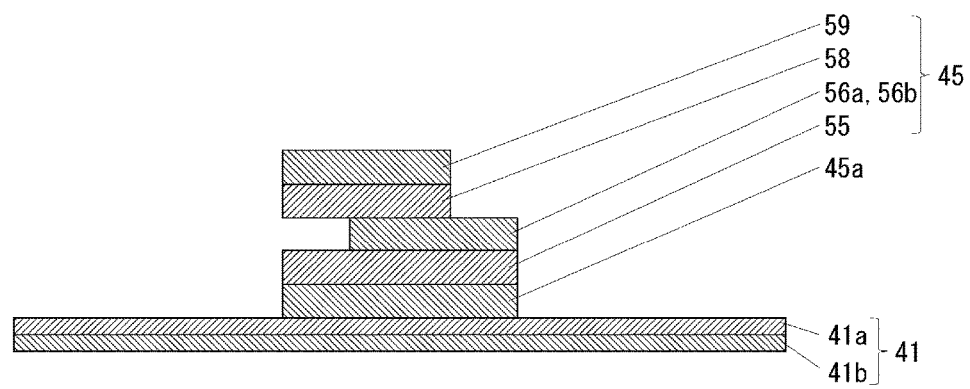
FIG. 4B is a sectional view illustrating an example of a configuration of the sensor element.
Figure 4C:
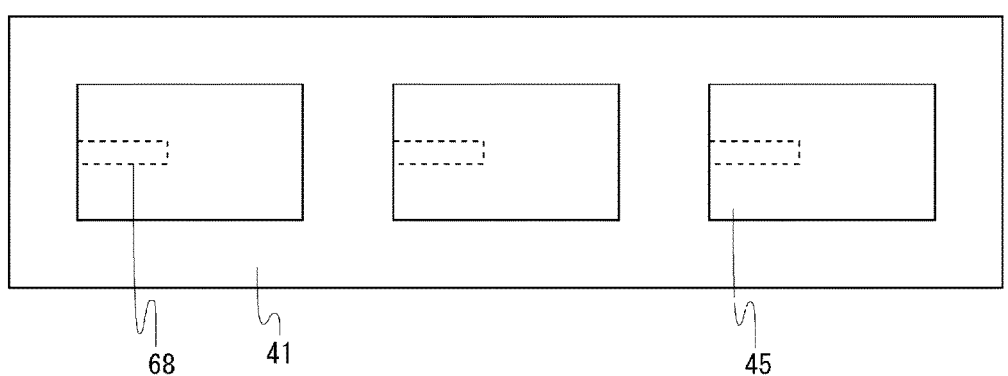
FIG. 4C is a top view of the example of the configuration of the sensor element.
Figure 5:
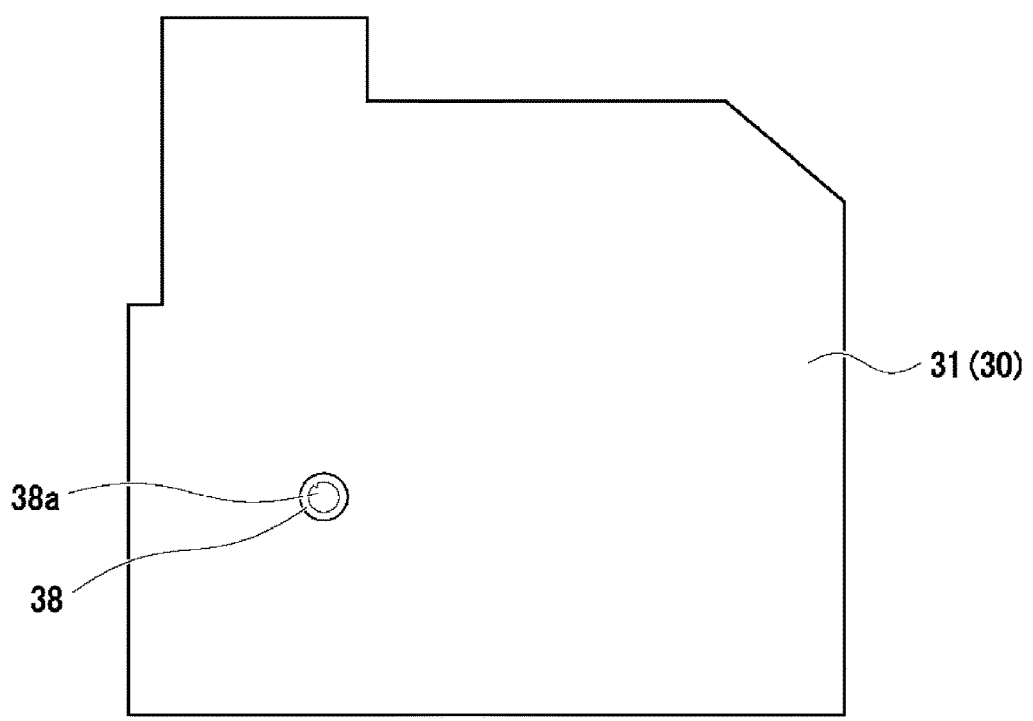
FIG. 5 is a view of an external appearance of a sensor cartridge.

To begin with, a configuration of a sensor cartridge 30 to be set in the measurement apparatus will be described with reference to FIGS. 2-5. Note that FIG. 2 in these drawings is a principal sectional view of principal portions of the measurement apparatus with the sensor cartridge 30 being set therein, the view being taken along a plane (passing through substantially a center of the slider knob 15a) orthogonal to a thicknesswise direction). FIG. 3 is a view of an external appearance of a reel hub 32 wound with a sensor element 40, the hub being housed in the sensor cartridge 30. FIG. 4A is an explanatory view illustrating an example of a configuration of a film-shaped sensor 45. FIG. 4B is a sectional view illustrating an example of a configuration of the sensor element 40. FIG. 4C is a top view of the sensor element 40. FIG. 5 is a view of an external appearance of the sensor cartridge 30 as viewed from the same side as in FIG. 2.

Figure 2:
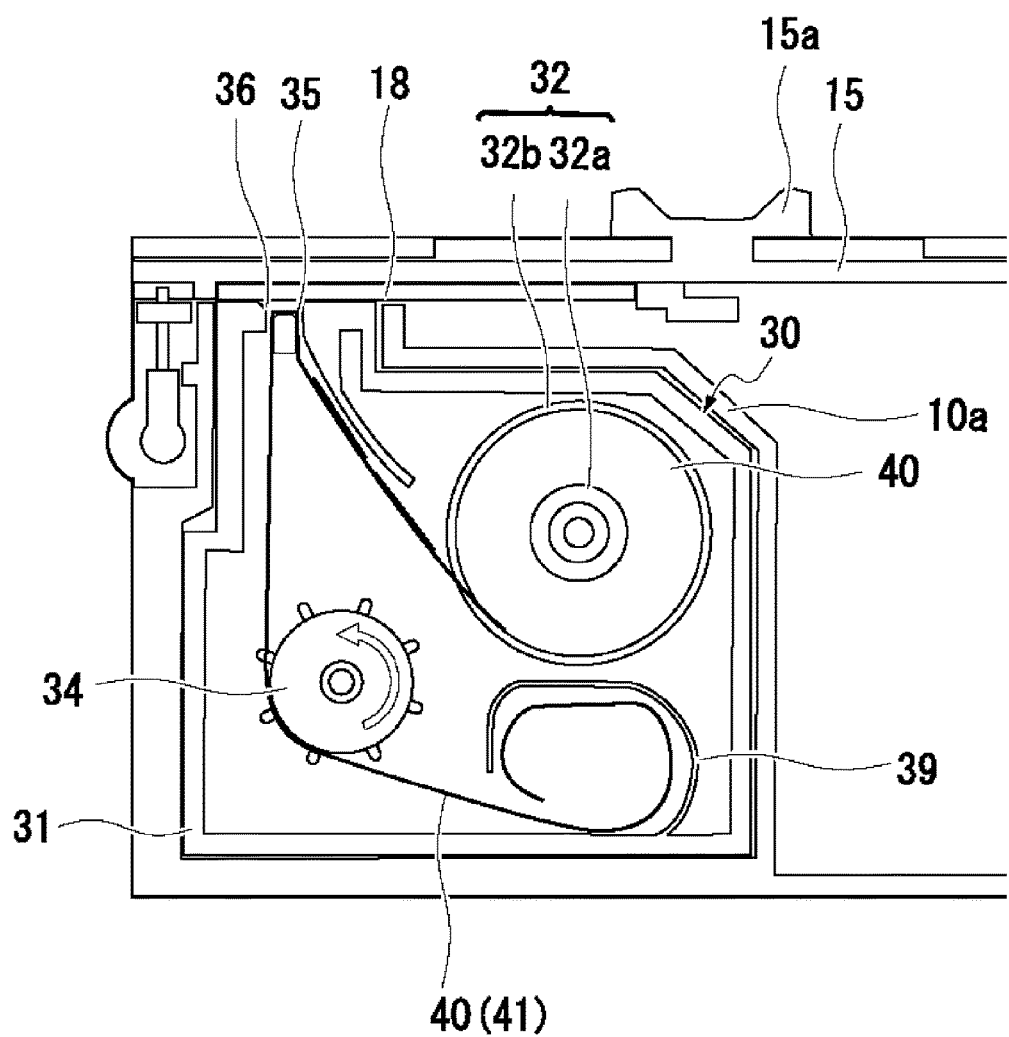
FIG. 2 is a principal sectional view of principal portions of the measurement apparatus according to the first embodiment, with a sensor cartridge being set therein, the view being taken along a plane orthogonal to a thicknesswise direction.

As apparent from the sectional view depicted in FIG. 2, the sensor cartridge 30 is configured by housing the reel hub 32 wound with the sensor element 40 in a case 31. The enclosure 10 of the measurement apparatus includes a cartridge housing unit 10a provided for housing the sensor cartridge 30.

The sensor element 40 (FIG. 3) is a tape-shaped member including a plurality of small-sized film-shaped sensors 45 bonded to amount film 41 by using a bonding material having a substantially weak bonding strength, the sensors 45 being at an approximate equal interval in a lengthwise direction of the film 41. Holes 42 each taking a rectangular shape with rounded corners are formed at the same interval as the interval (an interval between centers of the two neighboring film-shaped sensors 45, which will hereinafter be referred to as a sensor disposing interval) of disposing the film-shaped sensors 45 in portions with the film-shaped sensors 45 not being disposed.

The mount film 41 of the sensor element 40 is formed a film being is flexible but substantially hard to extend. Hence, the mount film 41 may involve using a resinous film, a laminated body of two or more types of resinous films, a laminated body of the resinous film and a metallic film, a body configured by embedding a metal wire or other equivalent material into the resinous film. However, the mount film 41 may have a hygroscopic property in order to restrain the film-shaped sensor 45 from deteriorating due to moisture. It is preferable in this case that the mount film 41 is formed of a material (the laminated body of the hygroscopic film and another film, and other equivalent materials) containing a hygroscopic substance.

Each of the film-shaped sensors 45 disposed on the mount film 41 is a sensor having, e.g., a configuration as schematically illustrated in FIG. 4A. To be specific, the film-shaped sensor 45 is, e.g., a sensor including: a substrate formed with an enzyme portion 57 to retain an enzyme reacting with a glucose, an electron acceptor and other equivalent chemical entities and with a plurality of electrodes 56a, 56b for detecting an oxidation reduction potential or an oxidation reduction current; a cover 59 stacked on the substrate 55, the cover being provided with a through-hole 59a via U-shaped spacer 58; and a flow path 68 for supplying a blood spotted on a front end portion thereof to the enzyme portion 57, the flow path 68 being defined by the substrate 55, the spacer 58 and the cover 59.

The sensor element 40 housed in the sensor cartridge 30 involves using a material enabling the film-shaped sensor 45 to be exfoliated from the mount film 41 when folded from a disposing surface of the film-shaped sensor 45 to be convexed. More specifically, the sensor element 40 involves using such a material that a bending stress exceeding the bonding strength to the mount film 41 occurs at the end portion of the film-shaped sensor 45 disposed on the bent portion when bending a portion with a certain film-shaped sensor 45 being disposed thereon at a curvature equal to or smaller than a predetermined curvature so that the disposing surface of the film-shaped sensor 45 is convexed.

The sensor element 40 meeting the specifications described above can be manufactured by adopting a configuration illustrated in, e.g., FIGS. 4B and 4C. In other words, the film-shaped sensor 45 involves using a laminated body configured by laminating a double-sided sheet tape serving as the spacer 58 and a hydrophilic film serving as the cover 59 on a PET (polyethylene terephthalate) sheet serving as the substrate 55 formed with the electrodes and other equivalent components. The mount film 41 involves using a laminated body configured by a base sheet (e.g., the PET sheet) 41a on a desiccant sheet (hygroscopic sheet) 41b, and an adhesive sheet (e.g., Easy peel sheet) 45a is used for bonding the film-shaped sensor 45 and the mount film 41 together.

The sensor element 40 having the configuration illustrated in FIGS. 4B and 4C can be manufactured by forming the laminated body, becoming the film-shaped sensor 45 on the mount film 41, with the film existing between the film-shaped sensors 45, and thereafter forming the hole 42 after half cutting and thus removing an unnecessary portion (between the film-shaped sensors 45) positioned more upward than the adhesive sheet up to a halfway point of the adhesive sheet (alternatively half cutting and thus removing the unnecessary portion positioned more upward than the adhesive sheet up to the halfway point of the adhesive sheet after forming the hole 42). Note that the half-cut can be attained by a pinnacle cutter, a Thomson cutter, a mold or a laser cutter and other equivalent cutters.

The sensor element 40 according to the first embodiment is, as apparent from FIG. 3, configured so that a width of each film-shaped sensor 45 is narrower than a width of the mount film 41, and each film-shaped sensor 45 is disposed at the central portion of the mount film 41 in a widthwise direction. The sensor element 40 can be therefore manufactured by half cutting and thus removing the unnecessary portions batchwise.

The reel hub 32 (FIGS. 2 and 3) wound with the sensor element 40 is a member configured by connecting two doughnut-shaped flanges 32b with a cylindrical portion 32a while inserting the cylindrical portion 32a through apertures formed in the central portions of the flanges 32b at an interval slightly wider than the width of the sensor element 40.

The reel hub 32 is housed in the case 31 in a state of being wound with the sensor element 40 when assembling the cartridge 30. Concretely, the case 31 is provided with a reel hub securing shaft extending in a thicknesswise direction (vertical to a sheet surface of FIG. 2) of the case 31 and having an outside diameter slightly smaller than an inside diameter of the cylindrical portion 32a of the reel hub 32. The reel hub 32 is housed in the case 31 in a way of inserting the reel hub securing shaft into the cylindrical portion 32a after winding the sensor element 40 along a periphery of the cylindrical portion 32a when assembling the cartridge 30.

Note that when winding the sensor element 40 on the reel hub 32 in a way of directing outward the surface provided with the film-shaped sensor 45, such a possibility occurs that the film-shaped sensor 45 existing at an outermost peripheral portion of the sensor element 40 wound on the reel hub 32 is exfoliated due to vibrations or other equivalent phenomena of the measurement apparatus. It is therefore preferable that the reel hub 32 is, as illustrated in FIG. 3, wound with the sensor element 40 in the way of directing inward the surface provided with the film-shaped sensor 45. FIG. 3 illustrates the sensor element 40 provided with the film-shaped sensors 45 up to a leading end of the mount film 41. However, the sensor element 40 wound on the reel hub 32 incorporated into the cartridge 30 is configured not to dispose the film-shaped sensor 45 at a portion (termed hereinafter a lead portion) having a predetermined length on the side of the leading end but to form the holes 42 at the disposing interval of the sensors.

A plurality of protrusions is provided along the reel hub securing shaft of the case 31 (FIG. 2), the protrusions engaging with the protrusions provided on the flange 32b on the side opposite to the case 31 to restrain the reel hub 32 from rotating in a winding direction of the sensor element 40.

The case 31 is provided with a roller securing shaft extending in a thicknesswise direction of the case 31. The case 31 houses a roller 34 enabled to rotate about the roller securing shaft, the roller 34 taking a cylindrical shape and including a plurality of pins disposed at an equal interval along an external surface thereof.

The pins of the roller 34 are inserted into the foregoing holes 42 (FIG. 3) of the sensor element 40. A diameter of the roller 34, a number of the pins disposed along the external surface of the roller 34 and the sensor disposing interval are determined so as to insert the pins into the holes 42 of the sensor element 40.

A fitting portion 38 taking a shape as illustrated in FIG. 5 is provided on the near side in FIG. 2 as viewed from the roller 34, the fitting portion 38 being configured to rotate together with the roller 34.

To be specific, the fitting portion 38 is provided on the near side of the roller 34, the fitting portion 38 being formed with a circular recessed portion 38a including a portion protruding toward the central side. The case 31 of the sensor cartridge 30 includes an aperture formed in a face-to-face portion with the fitting portion 38.

A sensor take-out port 35 and a film collecting port 36 are, as illustrated in FIG. 2, formed in a portion on a leading end side of a side wall, facing the slider 15, of the case 31. The sensor take-out port 35 serves as an aperture taking a shape admitting passage of the film-shaped sensor 45. The film collecting port 36 serves as an aperture taking a shape admitting passage of the mount film 41. The sensor take-out port 35 and the film collecting port 36 are provided at an interval shorter than a length of the film-shaped sensor 45. A shape of the side wall of the case 31 is determined so that "the sensor take-out port 35, the film collecting port 36 and a side wall portion existing therebetween" (which are hereinafter referred to as a port portion of the sensor cartridge 30) are recessed slightly more inward than other portions.

The case 31 also houses a curved surface wall 39 extending the thicknesswise direction of the case 31. A shape of this curved surface wall 39 is determined so that the sensor element 40 (the mount film 41) entering the portion not provided with the curved surface wall 39 is, as illustrated in FIG. 2, housed in a way of swirling within a film housing space defined by the curved surface wall 39.

The sensor element 40 in the sensor cartridge 30 passes through the sensor take-out port 35 and the film collecting port 36 and is, after being wound along the outer peripheral surface of the roller 34, collected within the film housing space. Note that the lead portion is housed within the film housing space in the sensor cartridge 30 before starting the use thereof.

A configuration and functions of the measurement apparatus according to the first embodiment will hereinafter be described.

Figure 6A:
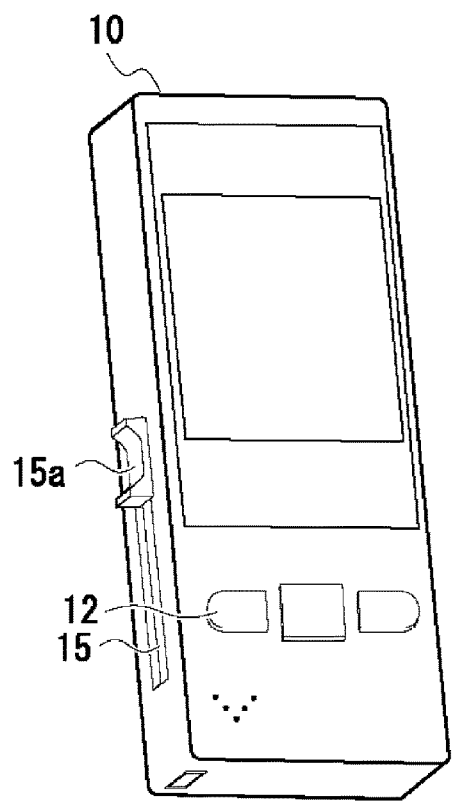
FIGS. 6A and 6B are explanatory views of functions of the measurement apparatus according to the first embodiment.
Figure 6B:
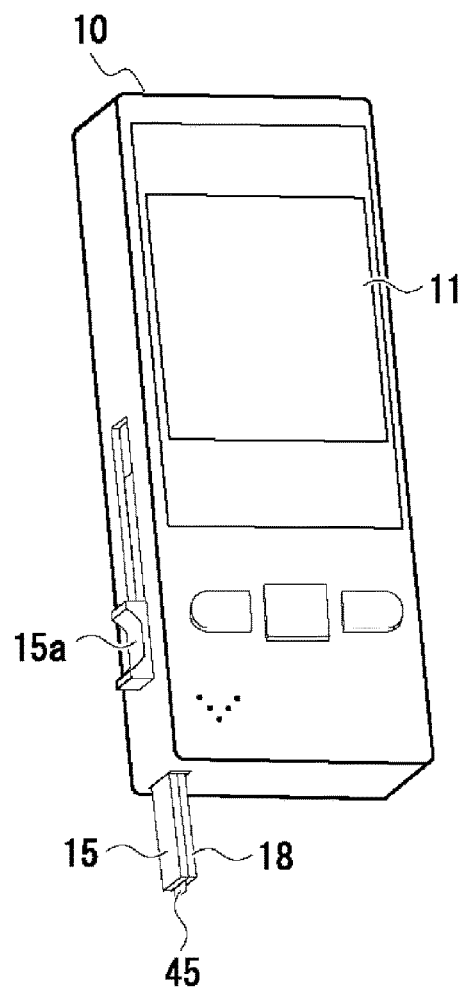

In the measurement apparatus according to the first embodiment, when in a standby mode (other than when measuring the blood glucose level), the slider knob 15a is located in a position illustrated in FIG. 1 (which will hereinafter be termed a standby position or a second position), i.e., located in the vicinity of a center of a slider movable range. The measurement apparatus according to the first embodiment is configured so that the slider knob 15a is, as illustrated in FIG. 6(A), temporarily slid to an uppermost position (which will hereinafter be termed a sensor take-out position or a third position), i.e., the vicinity of one end of the slider movable range, and is thereafter, as illustrated in FIG. 6(B), slid to a lowermost position (which will hereinafter be terms a measurement position or a first position), i.e., the end, vicinal to the aperture of the enclosure 10, of the slider movable range, with the result that the slider 15 and an auxiliary slider 18 protrude from an aperture (which will hereinafter be termed a slider protrusion port) formed in the enclosure 10 in a state of the film-shaped sensor 45 being pinched between tips of these sliders.

At first, a mechanical configuration of the measurement apparatus functioning when sliding the slider knob 15a to the sensor take-out position (the third position), will be described.

Figure 7:
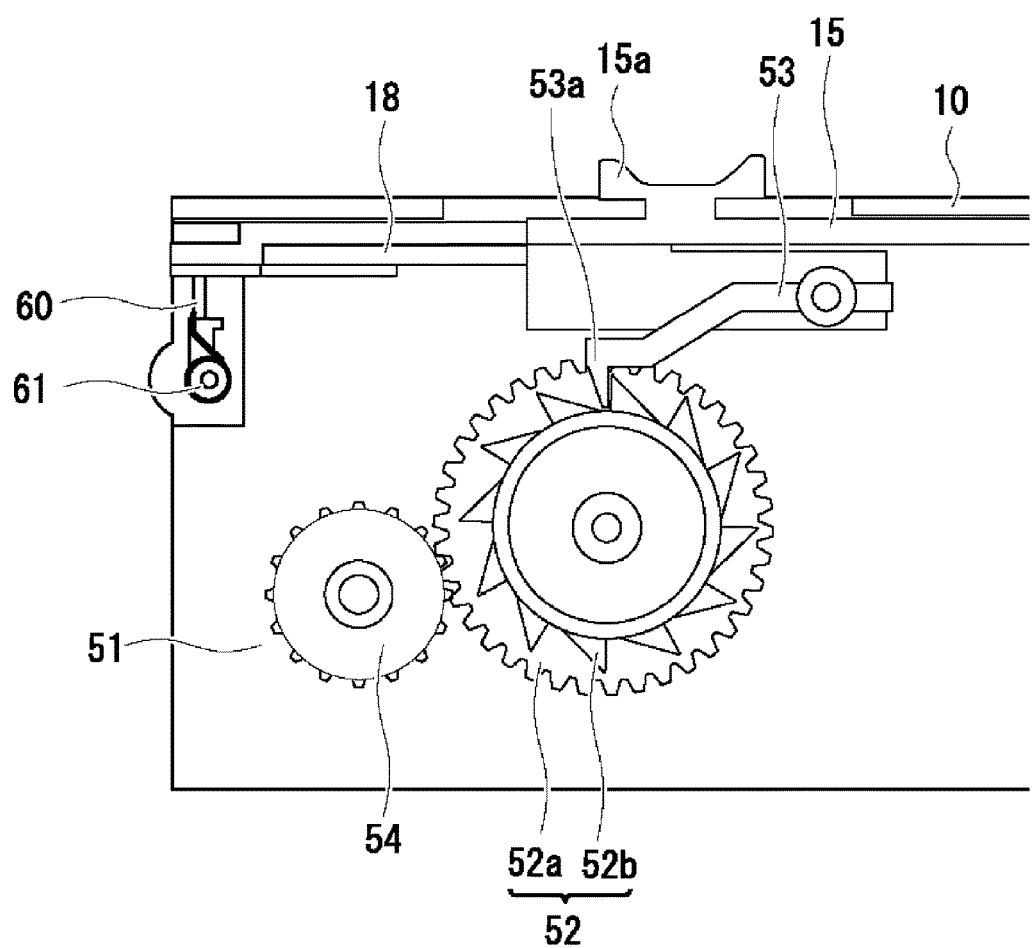
FIG. 7 is a sectional view taken in parallel to a front surface in the vicinity of the front side of the measurement apparatus according to the first embodiment.

FIG. 7 illustrates a sectional view taken in parallel to the front surface in the vicinity of the front side of the measurement apparatus according to the first embodiment.

As depicted in FIG. 7, the measurement apparatus includes a partition plate 51, a composite gear 52, a pawl member 53 and a driving gear 54. The partition plate 51 is a plate member with the sensor cartridge 30 being set on its undersurface (a surface on an invisible side in FIG. 7). The driving gear 54 is secured to the partition plate 51 so as to be rotatable about a rotary shaft thereof. The rotary shaft of the driving gear 54 is provided to penetrate the partition plate 51 in such a position as to be concentric with the fitting portion 38 of the roller 34 of the sensor cartridge 30 set in the enclosure 10. The rotary shaft of the driving gear 54 takes a shape matching with the fitting portion 38 (see FIG. 5) of the roller 34 of the sensor cartridge 30 when the sensor cartridge 30 is set therein.

The composite gear 52 is configured to include a general gear 52a and a general ratchet wheel 52b that are superposed in alignment of centers of rotations thereof. The composite gear 52 is rotatably secured to the partition plate 51. The rotary shaft of the composite gear 52 is positioned so that the gear 52a meshes with the driving gear 54. The pawl member 53 is a member fixed to the slider 15. The pawl member 53 includes a pawl 53a taking such a shape as to mesh with the ratchet wheel 52b of the composite gear 52 when the slider 15 is located in the standby position.

The shapes of the respective portions of the measurement apparatus according to the first embodiment and/or a moving distance from the standby position of the slider 15 to a sensor take-out position, are determined to satisfy the following two conditions.

[Condition 1] To attain a state where the slider 15 does not exist on the sensor take-out port 35 when the slider 15 moves to the sensor take-out position.

[Condition 2] To attain coincidence between "a value given by multiplying a radian angle of rotation of the roller 34 by a radius of the roller 34" and a value of the sensor disposing interval of the sensor element 40 (a value of the intervals between centers of the two adjacent film-shaped sensors 45 of the sensor element 40) when the slider 15 moves to the sensor take-out position from the standby position.

Figure 8:
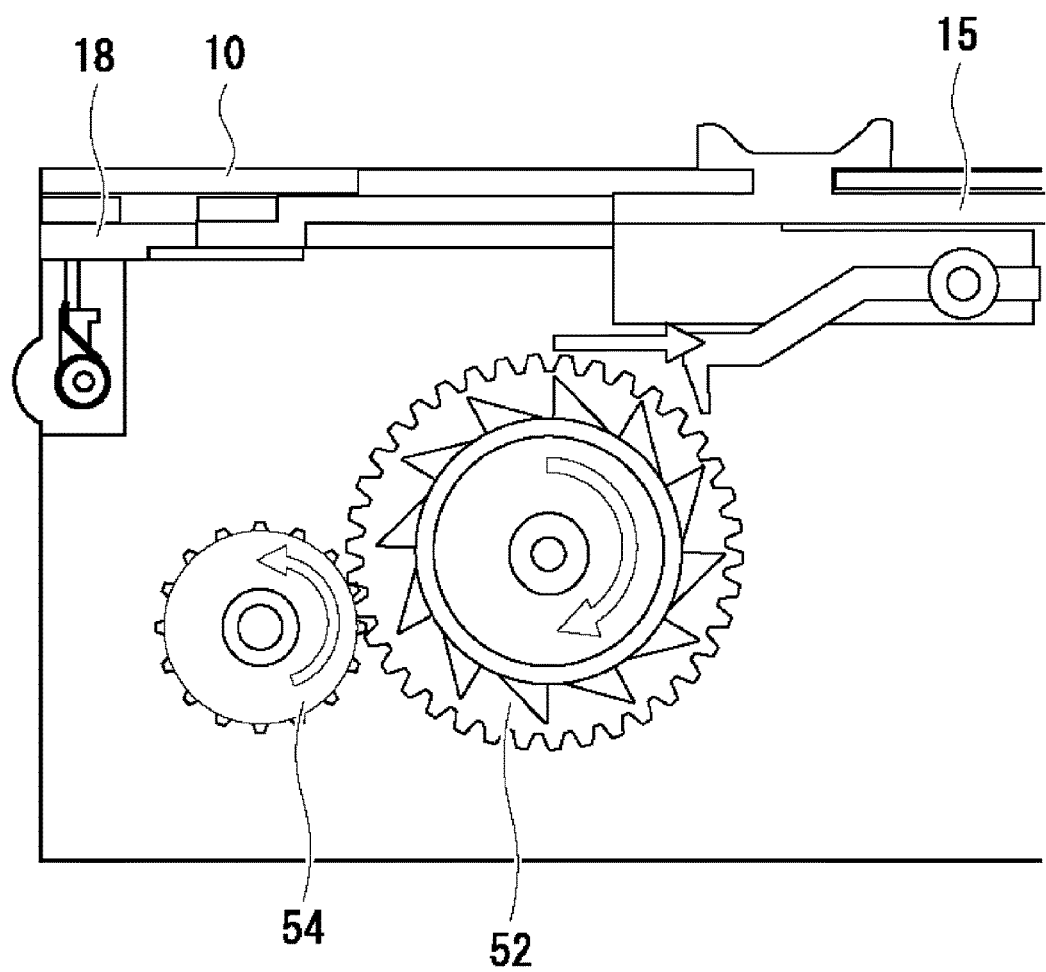
FIG. 8 is an explanatory view of operations of respective units of the measurement apparatus according to the first embodiment.

In short, as illustrated in FIG. 8, when the slider 15 moves to the sensor take-out position from the standby position by operating the slider knob 15a, the composite gear 52 rotates clockwise, while the driving gear 54 rotates counterclockwise. The rotary shaft of the driving gear 54 is fitted to the fitting portion 38, and hence the roller 34 rotates counterclockwise through the same angle as the angle of the driving gear 54. Accordingly, when determining the shapes and other equivalent data of the respective portions to attain the coincidence between "the value given by multiplying the radian angle of rotation of the roller 34 by the radius of the roller 34" and the value of the sensor disposing interval of the sensor element 40 when the slider 15 moves to the sensor take-out position from the standby position, the sensor element 40 within the sensor cartridge 30 can be fed by "the sensor disposing interval" in the direction of each film-shaped sensor 45 advancing toward the sensor take-out port 35.

Figure 9:
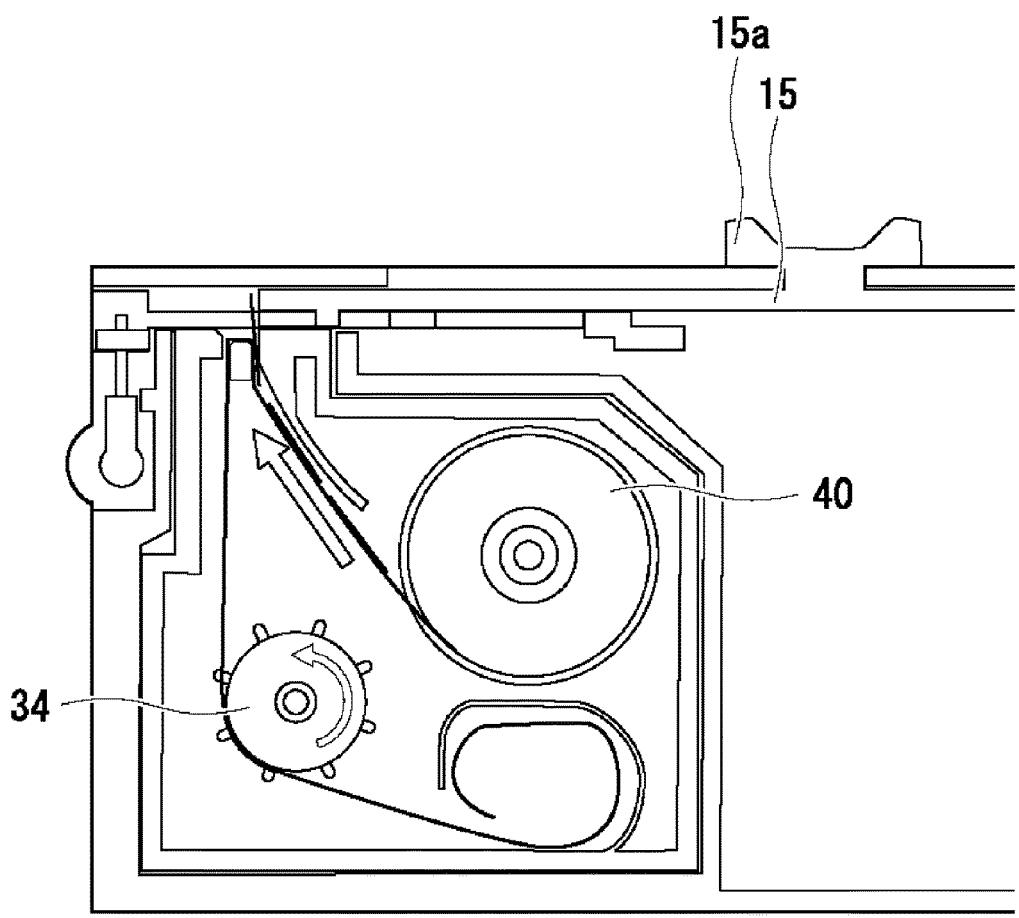
FIG. 9 is an explanatory view of the operations of the respective units of the measurement apparatus according to the first embodiment.
Figure 10:
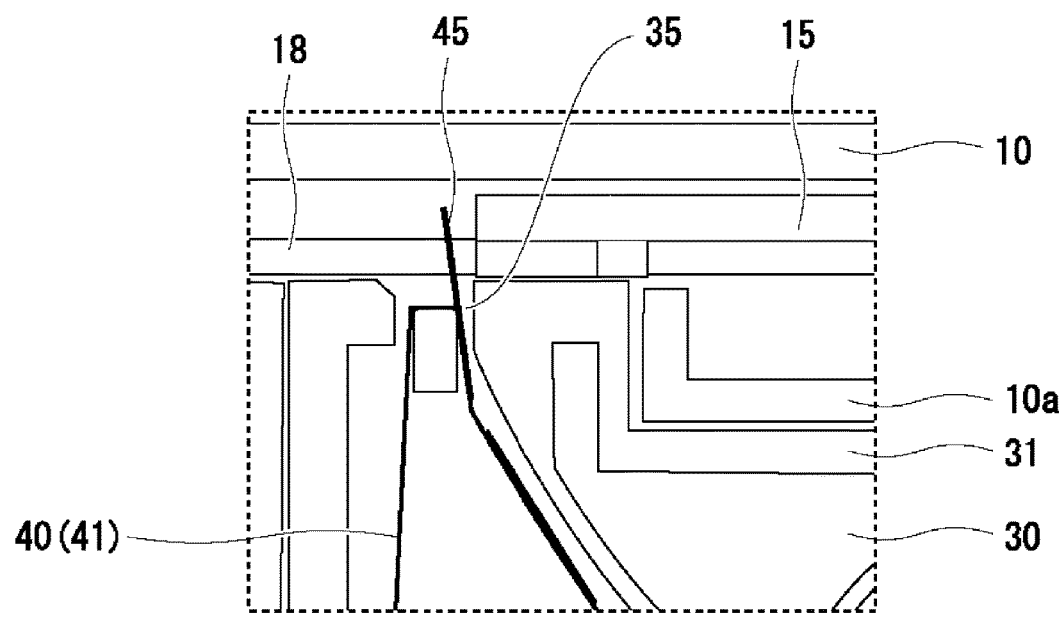
FIG. 10 is an explanatory view of the operations of the respective units of the measurement apparatus according to the first embodiment.

When the sensor element 40 is bent so that the surface, on which the film-shaped sensor 45 is disposed, of the sensor element 40 becomes convex, the film-shaped sensor 45 is exfoliated from the mount is exfoliated from the mount film 41. The sensor element 40 is consequently fed by "the sensor disposing interval". Upon reaching substantially 90-degree bending of the fed portion of the mount film 41 in the vicinity of an outlet of the sensor take-out port 35, the film-shaped sensor 45 adhered to the bent portion is exfoliated from the mount film 41. It follows then that the film-shaped sensor 45 protrudes from the sensor take-out port 35 as illustrated in FIGS. 9 and 10.

However, if the slider 15 is located above the sensor take-out port 35 when the film-shaped sensor 45 protrudes from the sensor take-out port 35, the slider 15 cannot carry the film-shaped sensor 45 protruding from the sensor take-out port 35. Therefore, the shapes and other equivalent data of the respective portions of the measurement apparatus are determined to satisfy the condition 1.

In the measurement apparatus according to the first embodiment, with the configuration described above, in linkage with retreating to the sensor take-out position (the third position) of the slider 15, the film-shaped sensor 45 is carried to the front of the tip of the slider 15 retreating to the sensor take-out position. It therefore follows that an aggregation of the pawl member 53 and the composite gear 52 to convert a rectilinear motion of the slider 15 into a rotary motion, and the driving gear 54 and the roller 34 within the sensor cartridge 30 to feed out the sensor element 40 by the rotating force of the composite gear 52, functions mainly as a "carrying mechanism" in the measurement apparatus according to the first embodiment.

Next, a mechanical configuration of the measurement apparatus functioning when the slider knob 15a is slid to the measurement position from the sensor take-out position, will hereinafter be described.

Figure 11:
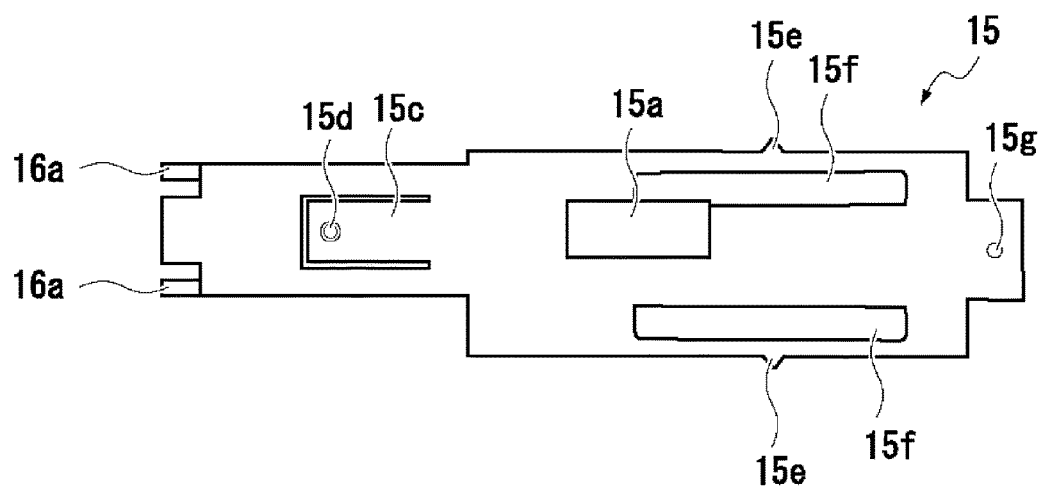
FIG. 11 is a view of an external appearance of a slider as viewed from the side of an upper surface.
Figure 12:
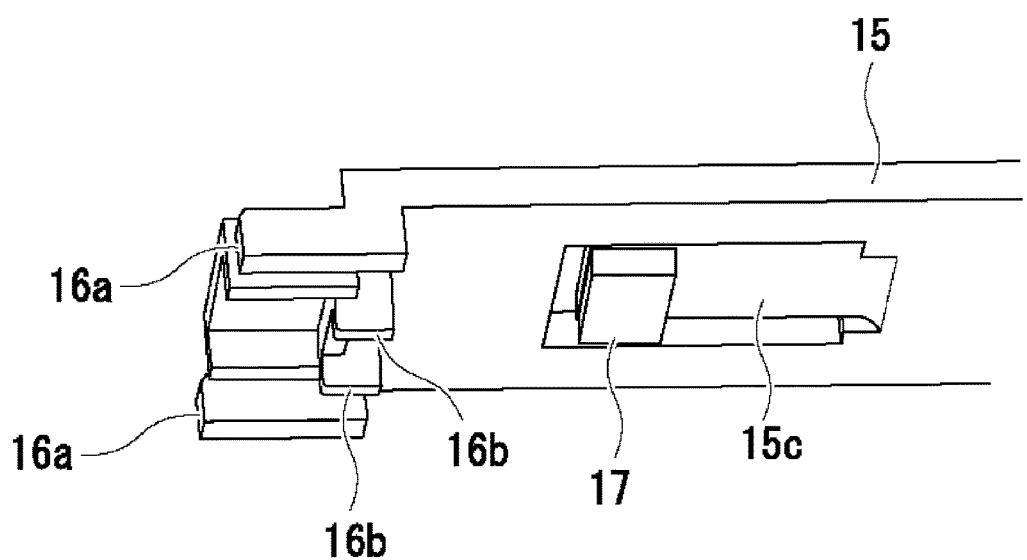
FIG. 12 is a view of an external appearance of the slider as viewed from the side of a lower surface.

FIG. 11 depicts a view of an external appearance of the slider 15 as viewed from the side of an upper surface (provided with the slider knob 15a). FIG. 12 illustrates a view of the external appearance of the tip of the slider 15 as viewed from the undersurface.

As illustrated in FIG. 12, two protrusions 16b for extruding forward the film-shaped sensor 45 protruding from the sensor take-out port 35 of the sensor cartridge 30, are provided at the center of the leading end of the slider 15. As depicted in FIGS. 11 and 12, structures 16a having shapes matching with structures provided at the leading end of the auxiliary slider 18 are provided on both sides of the leading end of the slider 15. The auxiliary slider 18 is herein disposed within the enclosure 10 to move together with the slider 15 as far as the slider 15 is located between the standby position and the measurement position.

A leading end of the auxiliary slider 18 is provided with a structure to pinch the film-shaped sensor in between the leading end of the slider 15 and the leading end of the auxiliary slider 18 in addition to the structure engaging with the structure 16a. When the slider 15 moves to the measurement position from the sensor take-out position by operating the slider knob 15a, at first, the film-shaped sensor 45 is extruded forward by the two protrusions 16b of the slider 15. Subsequently, the structure 16a provided at the leading end of the slider 15 is fitted to the structure provided at the leading end of the auxiliary slider 18, thereby forming a state of the film-shaped sensor 45 being pinched in between the leading end of the slider 15 and the leading end of the auxiliary slider 18 and also a state of the auxiliary slider 18 moving together with the slider 15. Then, these states remaining unchanged, when the slider 15 and the auxiliary slider 18 complete sliding to the measurement position of the slider knob 15a, as illustrated in FIG. 6(B), the film-shaped sensor 45 is held by the slider 15 and the auxiliary slider 18.

Figure 13:
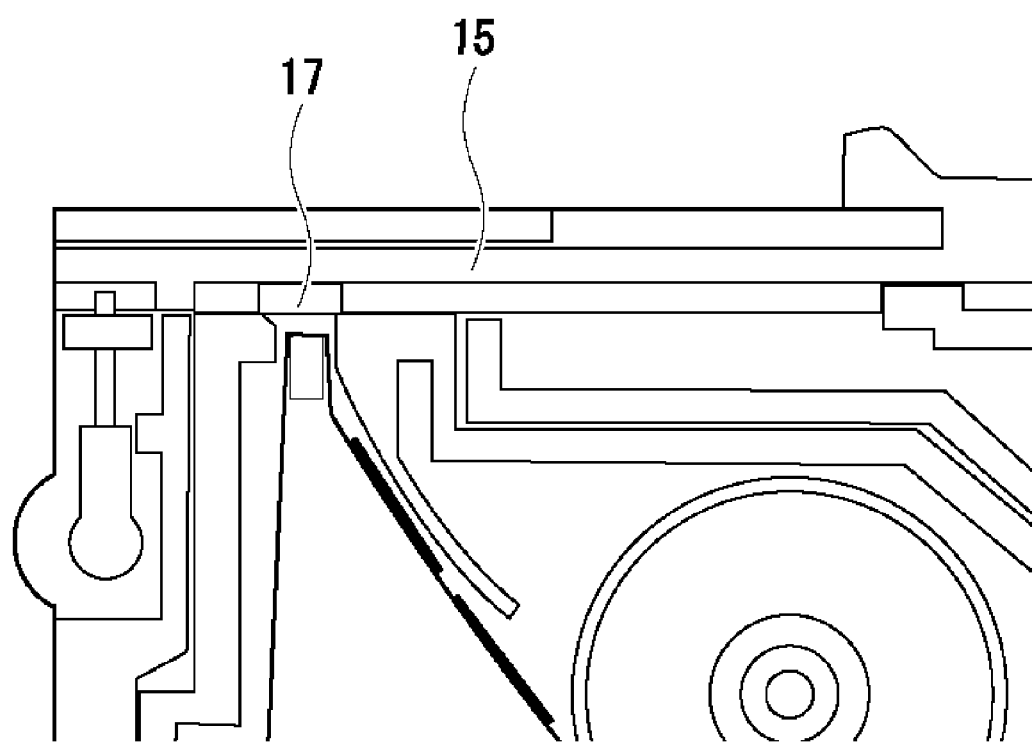
FIG. 13 is an explanatory view of a position of attaching a sealing rubber.

As depicted in FIGS. 11 and 12, the slider 15 includes a flexural portion 15c formed to enable the leading end (the left side in each drawing) to move vertically. A sealing rubber 17 is attached to an undersurface of the flexural portion 15c on the side of a leading end thereof. A position and a shape of the flexural portion 15c and a shape of the sealing rubber 17 are determined so that the sealing rubber 17, as illustrated in FIG. 13, is located above a port portion (configured by the sensor take-out port 35, the film collecting port 36 and a side wall therebetween) of the sensor cartridge 30 at least when the slider 15 is located in the standby position; and the flexural portion 15c and the sealing rubber 17 close the sensor take-out port 35 and the film collecting port 36, and seal the port portion of the cartridge 30 in the standby state. Note that the sealing rubber 17 may take a shape of flat sheet and preferably the same or similar shape as or to the shape of the port portion of the sensor cartridge 30.

As illustrated in FIG. 11, a protruded portion 15d taking a shape of circular truncated cone is provided at a portion, corresponding to substantially the center of the sealing rubber 17, of an upper surface of the flexural portion 15c. A hole 15g is formed in the central portion of the slider 15 on a tail end side (the right side in FIG. 11). A protruded portion 15e protruding in the widthwise direction is provided on each side surface of the slider 15 in the widthwise direction. The slider 15 is formed with an aperture 15f for facilitating flexure (displacement) of each protruded portion 15e in the widthwise direction of the slider 15.

Figure 14:
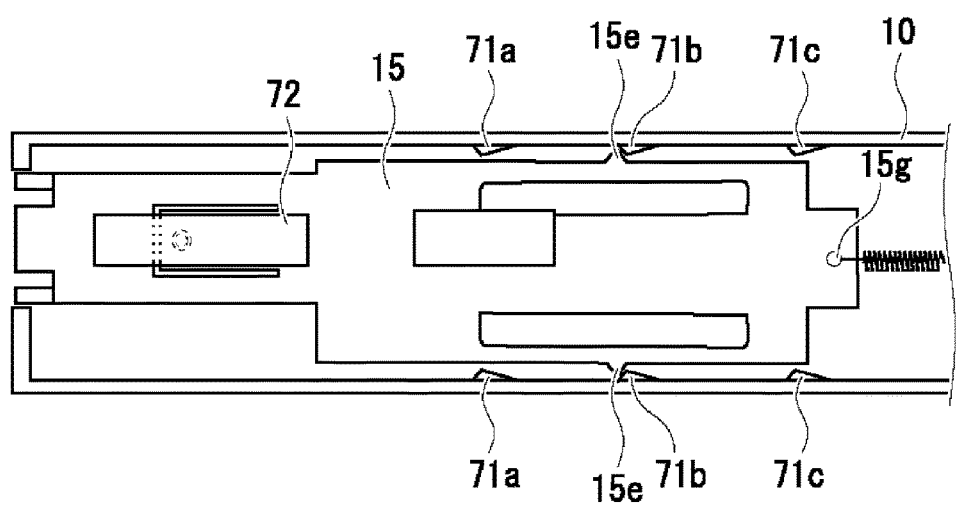
FIG. 14 is an explanatory view of a configuration of the measurement apparatus according to the first embodiment.

A coil spring establishes, as illustrated in FIG. 14, a connection between the hole 15g of the slider 15 and a specified portion within the enclosure 10. Three-tuple protruded portions 71x (x=a through c) are provided in positions depicted in FIG. 14 within the enclosure 10. To be specific, a couple of protruded portions 71a are provided within the enclosure 10, the protruded portions 71a serving to stop the slider 15 biased by the coil spring in the measurement position by engaging with a couple of protruded portions 15e of the slider 15. A couple of protruded portions 71b are further provided within the enclosure 10, the protruded portions 71b serving to stop the slider 15 in the standby position by engaging with the couple of protruded portions 15e of the slider 15. A couple of protruded portions 71c are still further provided within the enclosure 10, the protruded portions 71c serving to stop the slider 15 in the sensor take-out position by engaging with the couple of protruded portions 15e of the slider 15. As described above, each of the protruded portion 15e (corresponding to an engaging portion) of the slider 15 is a member flexible in the widthwise direction of the slider 15. It therefore follows that when applying force acting in the retreating direction to the slider 15 by operating the slider knob 15a, the protruded portion 15e becomes flexible to move over a protruded portion 71m (m=a, b) and engages with the next protruded portion 71.

A biasing means (a plate spring in FIG. 14) 72 is provided at a face-to-face portion with the protruded portion 15d of the slider 15 located in the standby position, the biasing means serving to push up the protruded portion 15d toward the port portion of the sensor cartridge 30. As already described, the sealing rubber 17 is provided on the underside of the protruded portion 15d. Therefore, when the slider 15 is located in the standby position, it follows that the port portion of the sensor cartridge 30 is sealed by the sealing rubber 17. Note that the sealing rubber 17 may not be used when the flexural portion 15c is firmly pressed down to tightly fit to the aperture (the port portion) of the censor cartridge 30.

Figure 15:
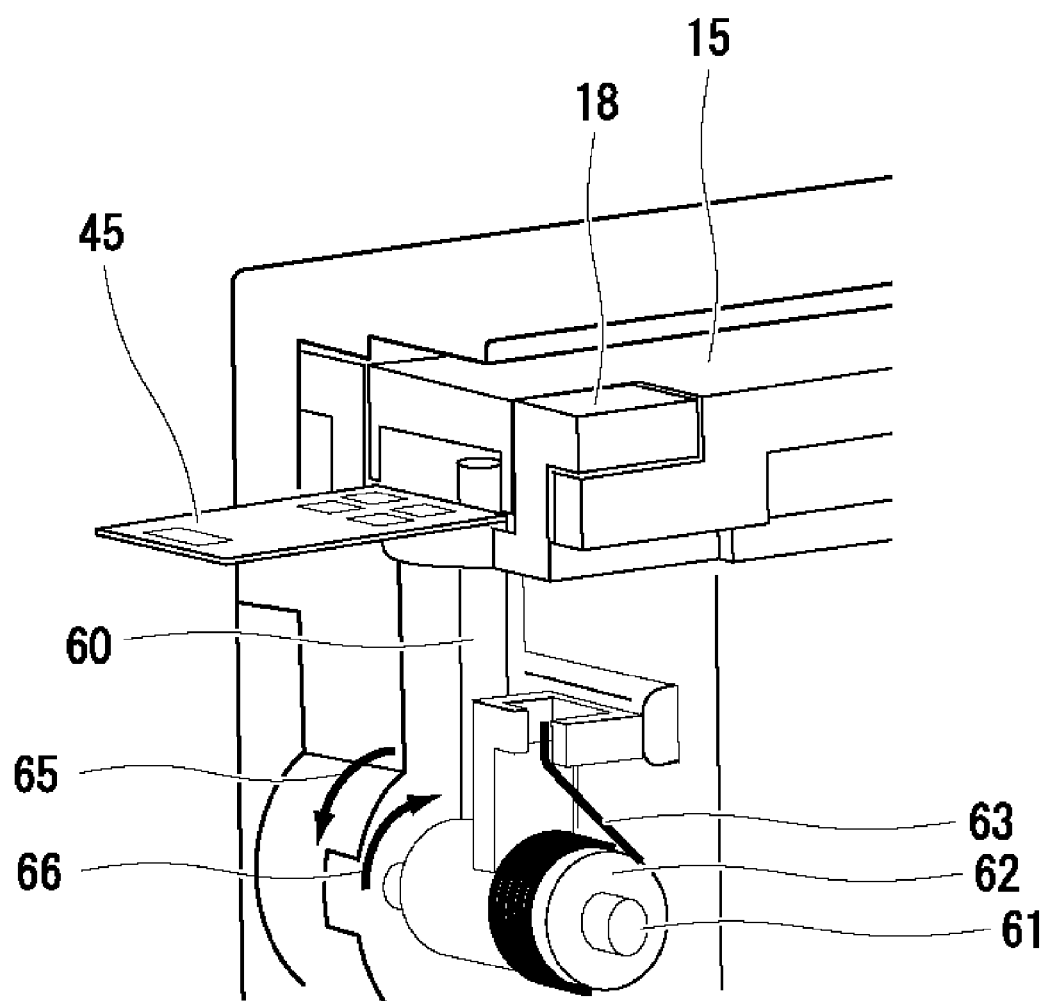
FIG. 15 is an explanatory view of a configuration of a sensor discard mechanism included in the measurement apparatus according to the first embodiment.

As illustrated in FIG. 15, a sensor discard mechanism is provided in the vicinity of a slider protrusion port (the aperture from which the slider 15 and the auxiliary slider 18 protrude) of the enclosure 10 of the measurement apparatus, the sensor discard mechanism (corresponding to a disengaging mechanism) including a discard pin 60, a rotary shaft 61, a rotary member 62 and a biasing member 63. The discard pin 60 of the sensor discard mechanism is fixed to the enclosure 10 and is parallel to the widthwise direction of the slider 15. The rotary member 62 rotates about the rotary shaft 61. The discard pin 60 is a rod-shaped member fixed to the rotary member 62 so as to be orthogonal to the rotary shaft 61. The biasing member 63 (the coil spring in FIG. 15) biases the discard pin 60 via the rotary member 62 in such a direction that the discard pin 60 becomes parallel to the undersurface of the enclosure 10.

As illustrated in FIG. 15, a length of the discard pin 60 of the sensor discard mechanism is determined so as to intersect a moving plane of the film-shaped sensor 45 in a state of being pinched in between the slider 15 and the auxiliary slider 18 when in parallel to the undersurface of the enclosure 10. A length of the discard pin 60 is further determined so as not to contact the respective portions (the portion existing between the two protrusions 16b, and other equivalent portions; see FIG. 12) of the slider 15. The leading end of the auxiliary slider 18 is formed with a groove through which the discard pin 60 passes.

In short, the discard pin 60 of the sensor discard mechanism is pushed by the film-shaped sensor 45 and falls down (see an arrowhead 65) when the film-shaped sensor 45 comes out of the slider protrusion port, and reaches a state in which a tip of this pin 60 slides on the undersurface of the film-shaped sensor 45. The discard pin 60 is, however, biased by the biasing member 63. Accordingly, once the film-shaped sensor 45 passes by, the discard pin 60 rises (see an arrowhead 66), and, as a result, such a state occurs that the tip of the discard pin 60 enters the auxiliary slider 18 and the slider 15. In this state, upon an operation to return the slider 15 to the standby position, the film-shaped sensor 45 used for the measurement abuts on the discard pin 60 before the slider 15 reaches the standby position. Then, the film-shaped sensor 45, upon abutting on the discard pin 60, comes to a state being disabled from moving, however, the slider 15 and the auxiliary slider 18 are slidable even when the discard pin 60 is erected. It therefore follows that the already-used film-shaped sensor 45 can be discarded simply by returning the position of the slider knob to the standby position after measuring the blood glucose level in the measurement apparatus including the sensor discard mechanism according to the first embodiment.

Next, an electrical configuration of the measurement apparatus will be described.

Figure 16A:
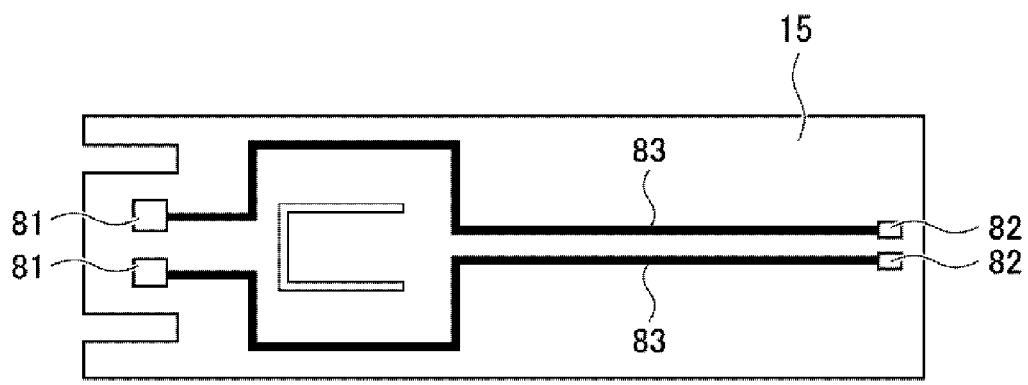
FIGS. 16A and 16B are explanatory views of an electrical configuration of the measurement apparatus according to the first embodiment.

An electrical configuration (circuit configuration) of the measurement apparatus according to the first embodiment is the same as the electrical configuration of the existing apparatus for measuring the blood glucose level and other equivalent measurement targets. When making the measurement, however, the measurement apparatus according to the first embodiment is configured to hold the film-shaped sensor 45 by the tip of the moving slider 15. The slider 15 is therefore provided with wires and other equivalent components for connecting the respective electrodes of the film-shaped sensors 45 to corresponding electrodes of the control unit 14 within the measurement apparatus. For example, when the film-shaped sensor 45 includes the two electrodes, as schematically illustrated in FIG. 16(A), the undersurface of the slider 15 is provided with electrodes 81 brought into contact with the respective electrodes of the film-shaped sensor 45, electrodes 82 connected to the control unit 14 (FIG. 10(B)) within the measurement apparatus and wires 83 for establishing connections between the electrodes 81 and the electrodes 82. Herein, the control unit 14 is a circuit using a processor (one-chip microcomputer and other equivalent processors) executing a process of measuring an oxidation reduction potential about the film-shaped sensor 45, a process of calculating the blood glucose level from a measurement result, and a process of controlling an LCD 11 (unillustrated) and the speaker 13. Note that the electrodes and the wires can be provided on the undersurface of the slider 15 by printing conductive materials on the undersurface of the slider 15, making use of in-mold forming (integrally molding the slider 15 and the electrodes/wires) and printing the conductive materials on the upper surface of the slider 15. The electrode 81 may also involve using a plate spring type electrode and a pin probe.

Figure 16B:
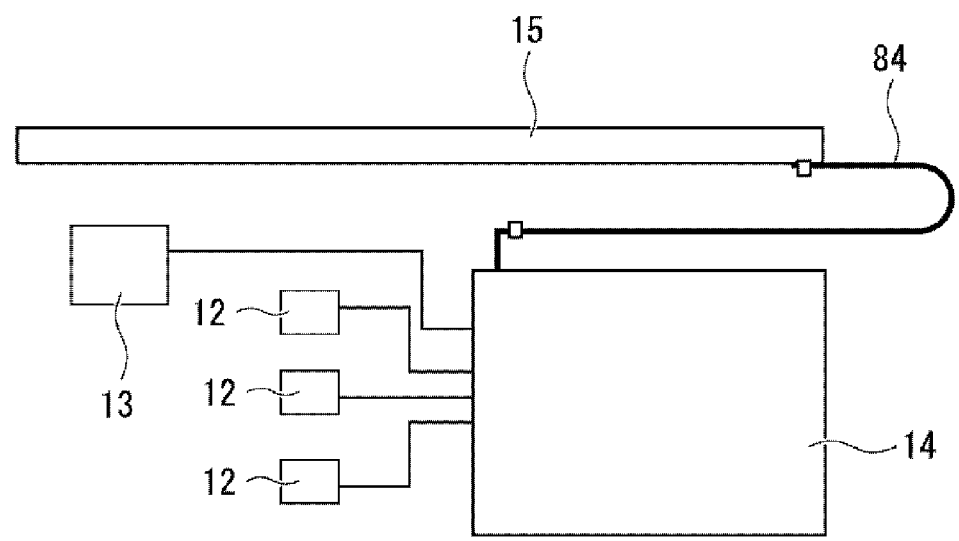

The measurement apparatus according to the first embodiment is configured so that the position of the slider 15 shifts within the apparatus, and hence it is considered that lead wires are entangled in the members within the measurement apparatus and result in being cut off when the respective electrodes 82 are connected via the lead wires to the control unit 14. Therefore, as schematically illustrated in FIG. 16(B), it is preferable that the electrodes 82 are connected to the control unit 14 by use of a flexible printed circuit board 84 or other equivalent components.

Each wire 83 (or each electrode 82) of the slider 15 may be configured to have a long portion parallel to the lengthwise direction of the slider 15; the enclosure-sided electrode may be fixed to the enclosure 10 to contact the wire 83 (or the electrode 82) irrespective of the position of the slider 15 per wire 83 (or per electrode 82); and the enclosure-sided electrode fixed to the enclosure 10 may be electrically connected to the control unit 14 via a cable or other equivalent connectors. The length of each wire 83 or each electrode 82 of the slider 15 and the position of the enclosure-sided electrode may be set so that each wire 83 or each electrode 82 contacts each enclosure-sided electrode as far as the slider 15 is located in the vicinity of the measurement position.

As discussed above, the measurement apparatus according to the first embodiment adopts a configuration that the slider 15 capable of advancing and retreating between a measurement position (a first position), a standby position (a second position) and a sensor take-out position (a third position), takes out a film-shaped sensor 45 from within the sensor cartridge 30, and the sensor 45 protrudes outside the enclosure 10. This configuration being adopted, the measurement apparatus according to the first embodiment has a small number of components (a decreased cost for manufacturing and assembling the components). The measurement apparatus according to the first embodiment can be therefore manufactured at the low cost.

In the measurement apparatus according to the first embodiment, the leading end of the film-shaped sensor 45 housed in the sensor cartridge 30 protrudes from the slider protrusion port (take-out port) of the enclosure 10 in a state of being held by the tips of the main slider 15 and the auxiliary slider 18. The user of the measurement apparatus according to the first embodiment can therefore apply a drop of blood to the film-shaped sensor 45 without being hindered by the enclosure 10 in spite of the small-sized film-shaped sensor 45. It is a sanitary aspect that the blood can be prevented from being spot-attached to the enclosure 10 when applying the drop of blood to the film-shaped sensor 45.

The measurement apparatus has the configuration enabling the film-shaped sensor 45 to be prepared through discarded simply by operating the slider knob 15*a*. When using all of the film-shaped sensors 45 in the sensor cartridge 30, a plurality of measurements is performed simply by replacing the sensor cartridge 30. It can be therefore said that the measurement apparatus according to the first embodiment is an apparatus exhibiting highly preferable operability.

The measurement apparatus according to the first embodiment is configured to enable the sensor cartridge 30 to be hermetically closed, the cartridge 30 not having any dedicated member for the hermetic closing. It follows that the measurement apparatus according to the first embodiment can provide the user with the sensor cartridge 30 being low in price to such a degree that the dedicated member for the hermetic closing may not be provided in the sensor cartridge 30.

The measurement apparatus according to the first embodiment is configured not to collect, into the measurement apparatus, the already-measured film-shaped sensor 45 to which a drop of analyte (blood) has been applied. It can be therefore said that the measurement apparatus according to the first embodiment can keep the interior of the apparatus in a sanitary state.

The measurement apparatus according to the first embodiment is configured not to require setting the glucose sensor (the film-shaped sensor 45) every time the blood glucose level is measured. The measurement apparatus is configured to perform applying the drop of blood to the film-shaped sensor 45 in an easy-to-apply position of the drop of blood in spite of using the small-sized film-shaped sensor 45, the position being slightly spaced away from the enclosure 10 of the measurement apparatus. It is also the sanitary aspect that the small-sized sensor can prevent the blood from being spot-attached to the enclosure 10 on the occasion of applying the drop of blood even when a protruded portion from the enclosure 10 is small in the state of setting the sensor in the measurement apparatus. Besides, the use of the measurement apparatus enables the film-shaped sensor 45 to be prepared through discarded simply by operating the slider knob 15a. When using all of the film-shaped sensors 45 in the sensor cartridge 30, the plurality of measurements is performed simply by replacing the sensor cartridge 30. It can be therefore said that the measurement apparatus according to the first embodiment is the apparatus exhibiting the highly preferable operability.

The measurement apparatus is configured not to collect, into the measurement apparatus, the already-measured film-shaped sensor 45 to which the drop of analyte (blood) has been applied, and can keep the interior of the apparatus in the sanitary state. The measurement apparatus is provided with the mechanism for sealing the sensor cartridge 30 on the side of the apparatus. The measurement apparatus being used, the sensor within the sensor cartridge 30 can be restrained from deteriorating due to a water content/outside air.

The measurement apparatus according to the first embodiment adopts such a configuration requiring the small number of components that the sealing rubber 17 fixed to the flexural portion 15c of the slider 15 for carrying the film-shaped sensor 45 housed in the sensor cartridge 30 outside the apparatus (the enclosure 10) hermetically closes the sensor cartridge 30 (seals the port portion of the sensor cartridge 30) when the apparatus is not used (when the slider 15 is located in the standby position). The measurement apparatus according to the first embodiment can be therefore manufactured at the substantially low cost. The measurement apparatus adopting the configuration described above, the sensor cartridge 30 for the measurement apparatus according to the first embodiment has no necessity for providing the dedicated member for the hermetic closing (i.e., the sensor cartridge 30 can be manufactured at the low cost). The measurement apparatus according to the first embodiment therefore enables the user to be provided with the sensor cartridge 30 as a consumable product at the low cost.

A description of a configuration of a sensor cartridge 30b developed to be set in the measurement apparatus according to the first embodiment will hereinafter be made with reference to FIG. 17 in a way of focusing on portions different from the sensor cartridge 30.

Figure 17:
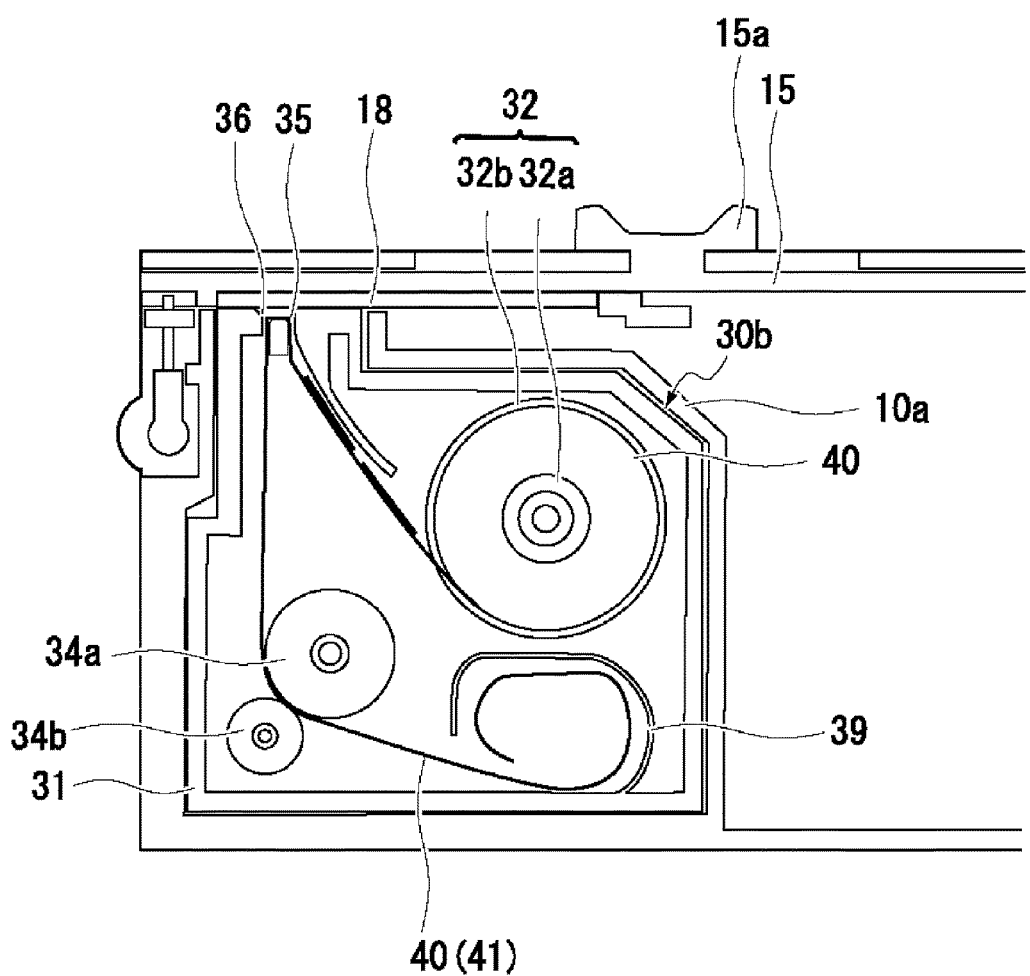
FIG. 17 is an explanatory view of a configuration of a sensor cartridge that can be set in the measurement apparatus according to the first embodiment.

As apparent from a comparison between FIG. 17 and FIG. 2, the sensor cartridge 30b has a configuration to replace the roller 34 of the sensor cartridge 30 with a roller 34a and a roller 34b.

The roller 34a does not include the plurality of pins provided on the external surface thereof. The roller 34b is a so-called pinch roller for press-fitting the mount film 41 onto the roller 34a.

In short, the sensor cartridge 30b has the configuration enabling a use of the sensor element 40 not formed with the holes 42 (FIG. 3). It can be therefore said that the sensor cartridge 30b can be manufactured at a lower cost than manufacturing the sensor cartridge 30 to such a degree as to eliminate a necessity for the process of forming the holes 42.

Second Embodiment

A configuration of the measurement apparatus according to a second embodiment of the present invention will be described by focusing on portions different from the measurement apparatus according to the first embodiment.

Figure 18:
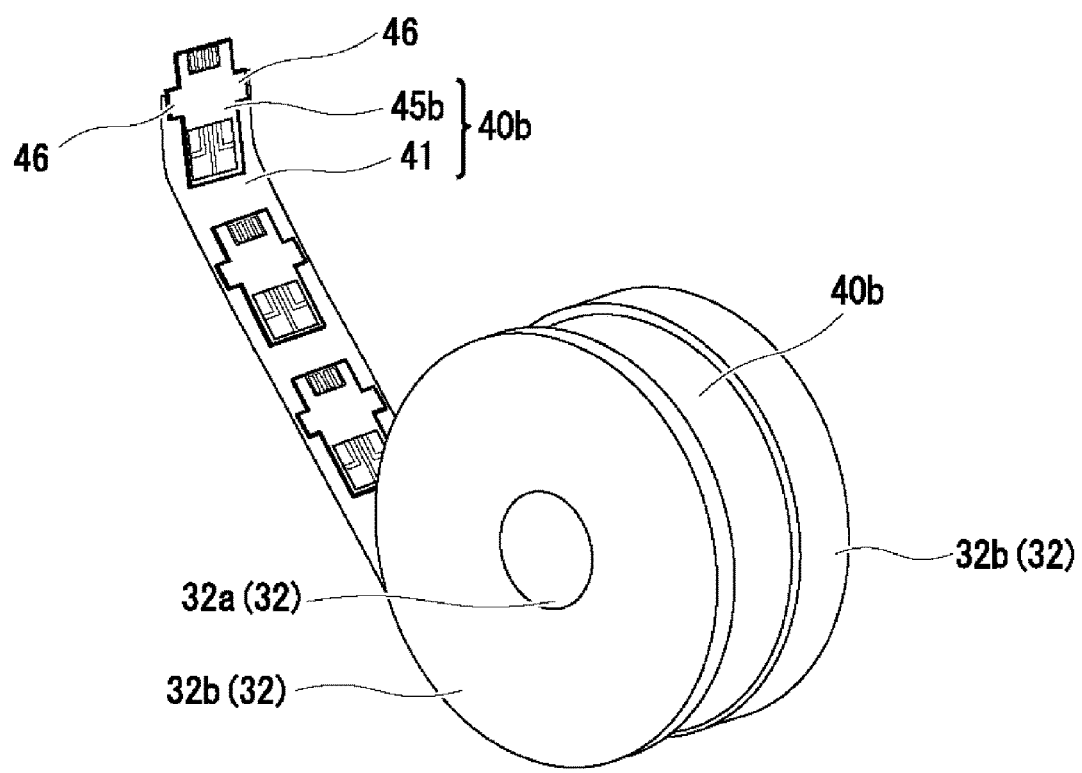
FIG. 18 is an explanatory view of a configuration of a sensor element used in the cartridge that is set in the measurement apparatus according to a second embodiment of the present invention.

The sensor cartridge according to the second embodiment, which is set in the measurement apparatus according to the second embodiment, is configured to include a sensor element 40b that replaces the sensor element 40 within the sensor cartridge 30b (FIG. 17), the sensor element 40b having a configuration illustrated in FIG. 18. The measurement apparatus according to the second embodiment of the present invention is configured as an apparatus different in terms of only the shape of the leading end of the slider 15 from the measurement apparatus according to the first embodiment.

To be specific, as depicted in FIG. 18, the sensor element 40b within the sensor cartridge according to the second embodiment is configured so that a plurality of film-shaped sensors 45b is provided with protruded portions 46 being slightly closer to the leading end than the central portion of both edges in the widthwise direction and is bonded onto the mount film 41 to parallelize the widthwise direction of each film-shaped sensor 45b and the widthwise direction of the mount film 41.

Each film-shaped sensor 45b taking the shape described above, the film-shaped sensor 45b protrudes from the sensor take-out port 35 of the sensor cartridge according to the second embodiment in a state of each protruded portion 46 being exfoliated from the mount film 41 (i.e., a state of enabling the member to be inserted under the lower edge of each protruded portion 46).

When setting beforehand the member to be inserted under the lower edge of each protruded portion 46 of the film-shaped sensor 45b protruding from the sensor take-out port 35, and even when the shape of the slider 15 and a positional relation between the respective portions are slightly different from a shape in design and a positional relation in design due to a manufacturing error or other equivalent errors, a part thereof enables the film-shaped sensor 45b adhered to the mount film 41 to be exfoliated form the mount film 41 and held by the slider 15.

The shape of the leading end of the slider 15 of the measurement apparatus according to the second embodiment is therefore designed so that the slider 15 can exfoliate the film-shaped sensor 45b from the mount film 41 and can hold the film-shaped sensor 45b by engaging with the lower edges of the two protruded portions 46 of the film-shaped sensor 45b protruding form the sensor take-out port 35.

Third Embodiment

A configuration and functions of the measurement apparatus according to a third embodiment of the present invention will hereinafter be described with reference to FIGS. 19A-19C.

The measurement apparatus according to the third embodiment is used by setting the sensor cartridge in the measurement apparatus in the same way as the measurement apparatuses according to the first and second embodiments. However, the measurement apparatus according to the third embodiment is configured to set and use a sensor cartridge 130 housing inside the plurality of film-shaped sensors 45 in the form of these sensors being stacked. Note that FIGS. 19A-19C depict the film-shaped sensor 45 in a size being large for the illustration's convenience, however, the small-sized film-shaped sensors 45 are housed in the sensor cartridge 130 set in the measurement apparatus according to the third embodiment.

Figure 19A:
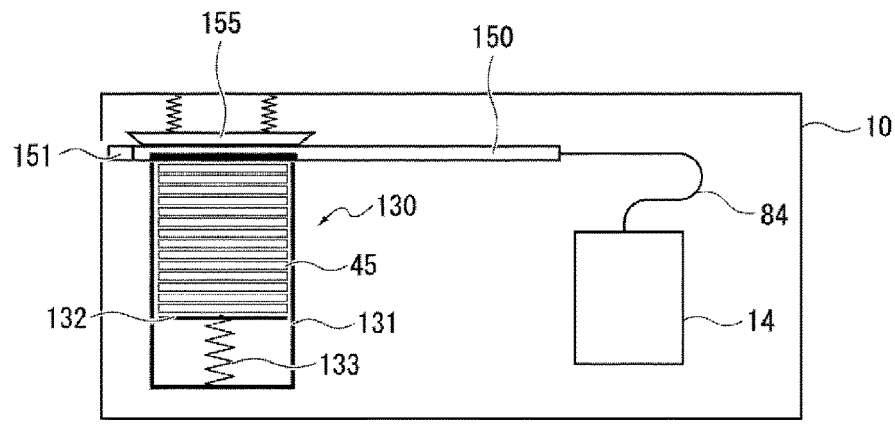
FIG. 19A is an explanatory diagram of a configuration and functions of the measurement apparatus according to a third embodiment of the present invention.
Figure 19B:
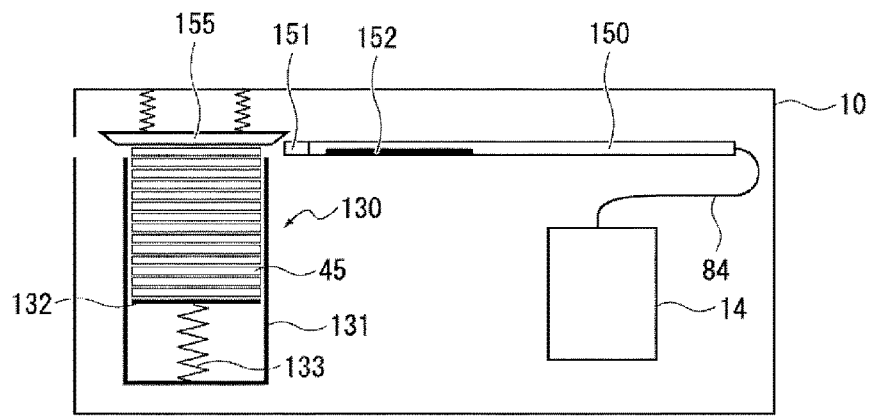
FIG. 19B is an explanatory diagram of the configuration and the functions of the measurement apparatus according to the third embodiment of the present invention.
Figure 19C:
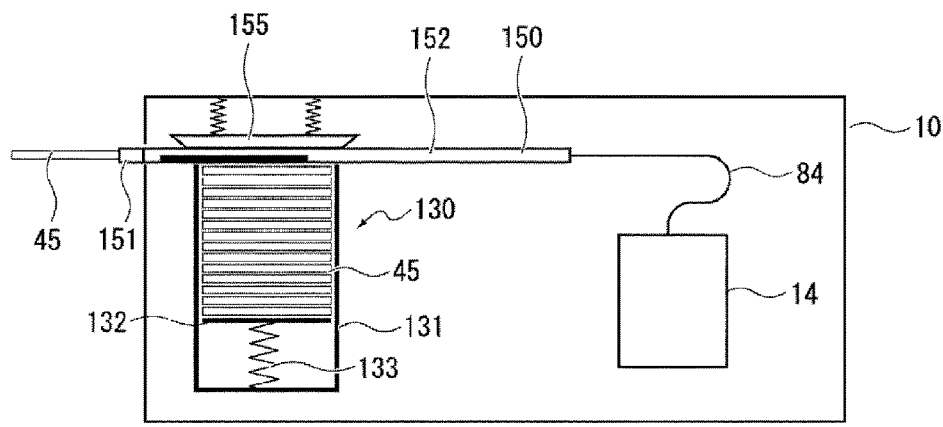
FIG. 19C is an explanatory diagram of the configuration and the functions of the measurement apparatus according to the third embodiment of the present invention.

As illustrated in FIGS. 19A-19C, the sensor cartridge 130 includes a case 131, a sensor mount plate 132 disposed within the case 131, and a biasing member 133 to bias the sensor mount plate 132 toward an aperture (an upper surface in FIGS. 19A-19C) of the case 131. The sensor cartridge 130 also includes the plurality of film-shaped sensors 45 stacked on the sensor mount plate 132.

Note that the sensor cartridge 130 is distributed to the user in a state of the aperture being sealed by a thin plastic film. When setting the sensor cartridge 130 in the measurement apparatus, the sensor cartridge 130 in the state of the aperture being sealed is set (housed) in a cartridge housing unit provided in the enclosure 10 of the measurement apparatus, and thereafter the plastic film covering the aperture is peeled off (pulled out).

The sensor cartridge 130 is set in the measurement apparatus in such a state that a slider 150 exists in a position (which will hereinafter be referred to as the standby position) depicted in FIG. 19. The slider 150 is a member that can be shifted between the standby position (the second position), the sensor take-out position (the third position) and the measurement position (the first position) by sliding the slider knob with its illustrated being omitted in the same way as the slider 15. Note that the sensor take-out position and the measurement position indicate the positions of the slider 150 illustrated in FIGS. 19B and 19C.

A tip of the slider 150 is provided with a connector 151 connectable to the film-shaped sensor 45. A sealing member 152 is provided at a face-to-face portion, to the aperture of the sensor cartridge 130 (the case 131), of the slider 150 when located in the standby position, the sealing member 152 taking a shape covering the aperture of the sensor cartridge 130 and being composed of a material (rubber and other equivalent materials) having elasticity. A flexural structure or other equivalent structures for facilitating tight fitting to the port portion may also be provided at a face-to-face portion, to the port portion of the sensor cartridge 130 (the case 131), of the slider 150 when located in the standby position. Further, the slider 150 is formed with wires and other equivalent members for establishing electric connections between respective electrodes of a connector 151 and respective electrodes of the control unit 14 via the flexible printed circuit board 84.

The measurement apparatus includes a pressing member 155 biased by the coil spring toward the sensor cartridge 130. The pressing member 155 functions as a member for pressing the sealing member 152 of the slider 150 against the aperture of the sensor cartridge 130 when the slider 150 is located in the standby position (FIG. 19A). However, the pressing member 155 functions as the member for causing the film-shaped sensor 45 to protrude by a proper quantity from the aperture of the sensor cartridge 130 when the slider 150 is located in the sensor take-out position (FIG. 19B). Note that the proper quantity connotes such a quantity that the film-shaped sensor 45 is set to the connector 151 of the slider 150 being on movement to the measurement position from the sensor take-out position.

As discussed so far, the measurement apparatus according to the third embodiment also adopts the configuration that the slider 15 capable of advancing and retreating between the measurement position (the first position), the standby position (the second position) and the sensor take-out position (the third position), takes out the sensor 45 from within the sensor cartridge 130, and the sensor 45 protrudes outside the enclosure 10. The measurement apparatus according to the third embodiment can be therefore manufactured at the low cost similarly to the measurement apparatuses in the first and second embodiments described above.

The measurement apparatus according to the third embodiment is configured so that the slider 150 protrudes from the slider protrusion port of the enclosure 10 in the state where the tip (the connector 151) of the slider 150 holds the film-shaped sensor 45 housed in the sensor cartridge 130. The user of the measurement apparatus according to the third embodiment can therefore apply the droplet to the film-shaped sensor 45 without being hindered by the enclosure 10 in spite of the small-sized film-shaped sensor 45.

The measurement apparatus according to the third embodiment is also configured not to have the necessity for providing the mechanism for the hermetic closing on the side of the sensor cartridge 130 similarly to the measurement apparatuses according to other embodiments. The measurement apparatus according to the third embodiment can provide the user with the sensor cartridge 130 as the consumable product at the low cost.

The measurement apparatus according to the third embodiment can easily (without being hindered by the enclosure 10 of the measurement apparatus) apply the drop of blood to the sensor 45 in spite of using the small-sized sensor 45, and can prevent the blood from being attached to the enclosure similarly to the apparatuses according to other embodiments. The measurement apparatus according to the third embodiment includes the mechanism for sealing the sensor cartridge 130, the mechanism being provided on the side of the apparatus. Accordingly, the measurement apparatus according to the third embodiment being used, it follows that the sensor within the sensor cartridge 130 can be restrained from deteriorating due to the water content/outside air without increasing the price of the sensor cartridge 130.

The measurement apparatus according to the third embodiment adopts a configuration that the pressing member 155 presses the slider 150 for carrying the sensor 45 housed so far within the sensor cartridge 130 outside the apparatus (the enclosure 10), thereby hermetically closing the sensor cartridge 130 (sealing the aperture of the sensor cartridge 130) when the apparatus is not used (when the slider 150 is located in the standby position). This configuration leads to a decreased number of components similarly to the measurement apparatuses according to other embodiments. The measurement apparatus according to the third embodiment can be therefore manufactured at the substantially low cost.

Fourth Embodiment

A configuration and functions of the measurement apparatus according to a fourth embodiment of the present invention will hereinafter be described with reference to FIGS. 20A-20C.

The measurement apparatus according to the fourth embodiment is also configured to measure the blood glucose level by using the small-sized film-shaped sensor 45 similarly to the measurement apparatuses according to the first, second (and third) embodiments. However, the measurement apparatus according to the fourth embodiment is configured as an apparatus used by directly setting the film-shaped sensor 45.

Figure 20A:
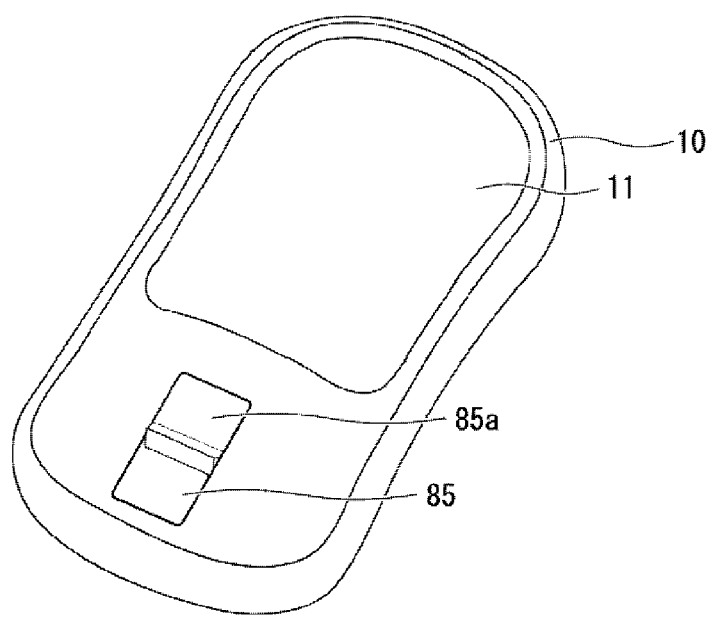
FIG. 20A is an explanatory diagram of a configuration and functions of the measurement apparatus according to a fourth embodiment of the present invention.
Figure 20B:
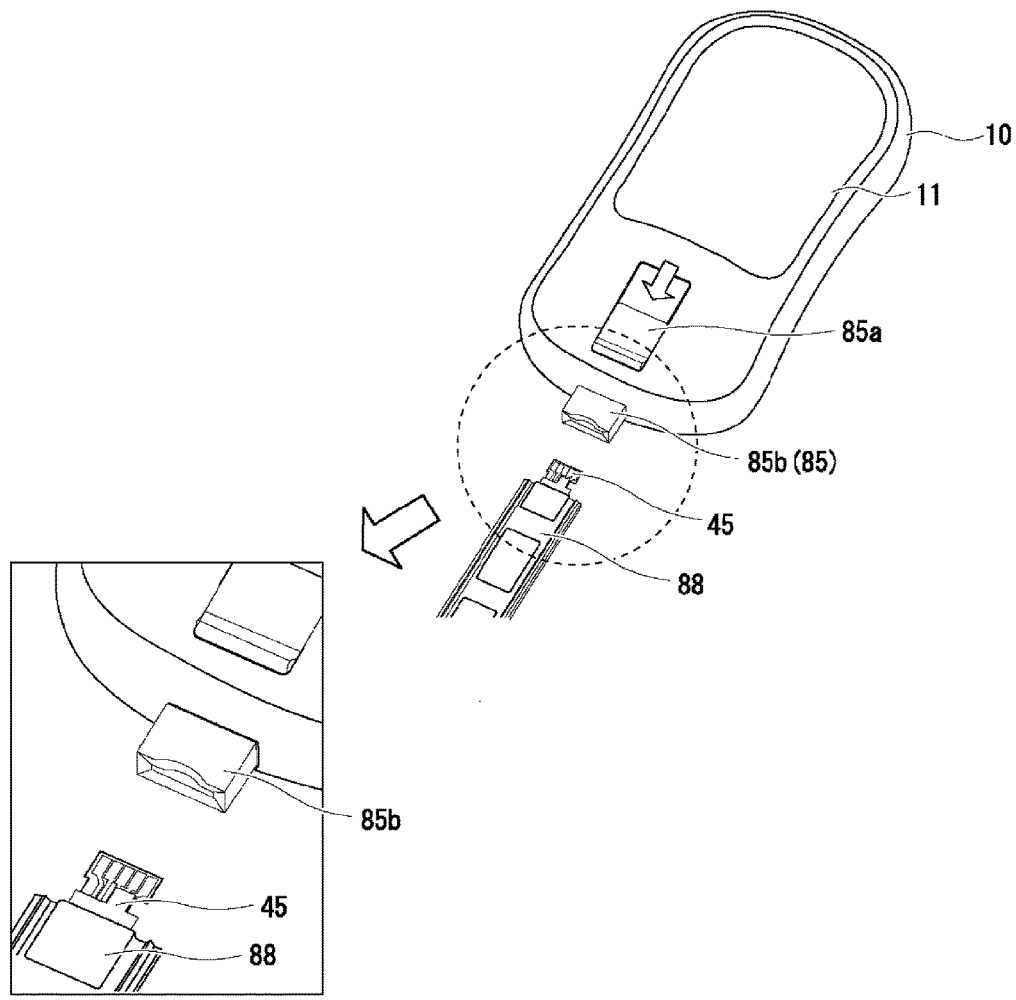
FIG. 20B is an explanatory diagram of the configuration and the functions of the measurement apparatus according to the fourth embodiment of the present invention.
Figure 20C:
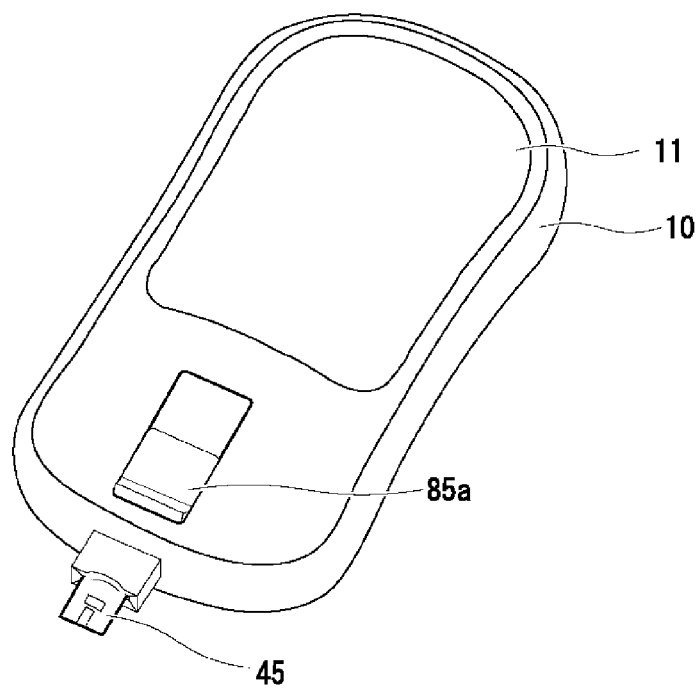
FIG. 20C is an explanatory diagram of the configuration and the functions of the measurement apparatus according to the fourth embodiment of the present invention.

To be specific, as illustrated in FIGS. 20A-20C, the measurement apparatus according to the fourth embodiment is a non sensor built-in type apparatus not having the built-in sensor cartridge, the sensor being set by the user every time the measurement is made. The measurement apparatus includes the enclosure 10 and an LCD 11 disposed on the front surface of the enclosure 10. The measurement apparatus further includes a slider knob 85a and slidable in the vertical direction, and a slider 85 moving together with the slider knob 85a, the knob and the slider being disposed on the front surface of the enclosure 10. Note that a plurality of push button switches is provided on a side surface, concealed in FIGS. 20A-20C, of the enclosure 10 of the measurement apparatus according to the fourth embodiment. The enclosure 10 incorporates the control unit having the same configuration and function as the foregoing control unit 14 has.

The tip of the slider 85 is provided with a connector 85b connectable to the film-shaped sensor 45. Electrodes of the connector 85b are electrically connected to the control unit of the measurement apparatus according to the third embodiment by the same connecting method as described by use of FIG. 16. The connector 85b is housed within the enclosure 10 when the slider knob 85a is located in the position (which will hereinafter be referred to as the standby position) depicted in FIG. 20.

When measuring the blood glucose level by using the measurement apparatus according to the fourth embodiment, the user at first slides the slider knob 85a located in the standby position to the measurement position (the position depicted in FIG. 20B).

Upon this operation, the connector 85b of the slider 85 protrudes from the aperture formed in the enclosure 10 (FIG. 20B), and the user sets the film-shaped sensor 45 in the connector 85b. On this occasion, the connector is in a protruded state, and hence the sensor can be easily set in the connector even when the sensor is small.

Note that the film-shaped sensor 45 is of the small size. Therefore, in the measurement apparatus according to the fourth embodiment, the film-shaped sensor 45 may also be set in the connector 85b by using a jig 88 for facilitating the operation of setting the small-sized film-shaped sensor 45 in the connector 85b.

Thereafter, the user performs the operation of applying the drop of blood to the film-shaped sensor 45 set in the connector 85b. However, as illustrated in FIG. 20C, in the measurement apparatus according to the fourth embodiment, when setting the film-shaped sensor 45 in the connector 85b, the film-shaped sensor 45 is located in a place spaced slight away from the enclosure 10 of the measurement apparatus.

Accordingly, it follows that the use of the measurement apparatus according to the fourth embodiment facilitates applying the drop of blood to the small-sized film-shaped sensor 45 in the same way as using the measurement apparatuses according to the first, second (and third) embodiments. It is the sanitary aspect that the blood is prevented from being attached to the enclosure 10 of the measurement apparatus when applying the drop of blood thereto.

Modified Example

The plurality of technologies described above may be modified in a variety of forms. For example, the sensor element 40b within the sensor cartridge according to the second embodiment may be modified into the sensor element 40 formed with the holes 42 at the sensor disposing interval as illustrated in FIG. 3. The desiccant may also be contained in each sensor cartridge.

Each of the measurement apparatuses described above involves using the slider as a moving member, and includes the film-shaped sensor 45 that protrudes in the state being pinched in between the slider 15 and the auxiliary slider 18. Each measurement apparatus may, however, be modified into an apparatus not including the auxiliary slider 18. Note that the modification of each measurement apparatus into the apparatus not including the auxiliary slider 18 may be attained by adopting the following configuration. The film-shaped sensor 45 is inserted into the tip of the slider 15 and can be thereby fixed, and there is provided a connector enabling the electrical connection to be established between the film-shaped sensor 45 and the control unit 14. Further, the flexibility is given to the tip (in the vicinity of the connector) of the slider 15. The measurement apparatus is provided with a biasing mechanism for moving the tip of the slider 15 toward the sensor cartridge 30 when passing by above the sensor take-out port 35.

After the slider 150 of the measurement apparatus according to the third embodiment has been modified into a slider including an aperture formed in the central portion of the tip thereof, the same mechanism as the sensor discard mechanism (FIG. 15) equipped in the measurement apparatuses according to the first and second embodiments may also be added to the measurement apparatus according to the third embodiment.

Figure 21:
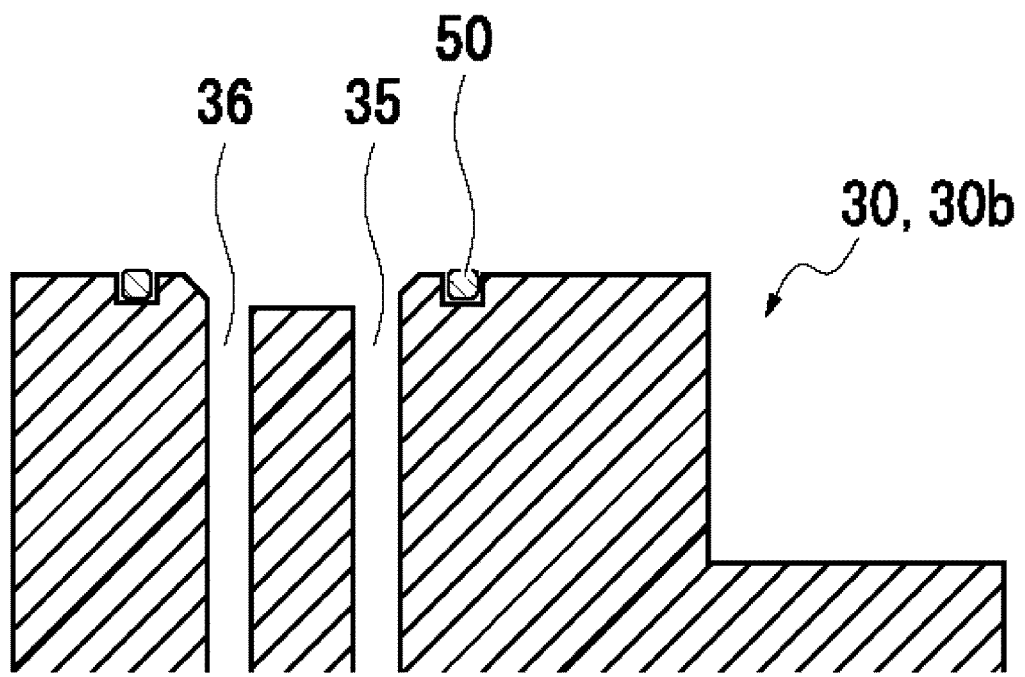
FIG. 21 is an explanatory diagram of a technology adoptable for improving a hermetic closing property of the sensor cartridge.

The elastic member 50 taking the shape of closed curve may also be, as schematically illustrated in FIG. 21, disposed to surround the port portion of each of the sensor cartridges 30, 30b in order for the sealing rubber 17 to seal (hermetically close) the sensor cartridges 30, 30b further preferably. As a matter of course, the elastic member taking the shape of closed curve may also be disposed to surround the aperture ("the port portion formed with the sensor protrusion port" in the sensor cartridge 130) of the censor cartridge 130 in order for the sealing member 152 to seal the sensor cartridges 130 further preferably.

Figure 22:
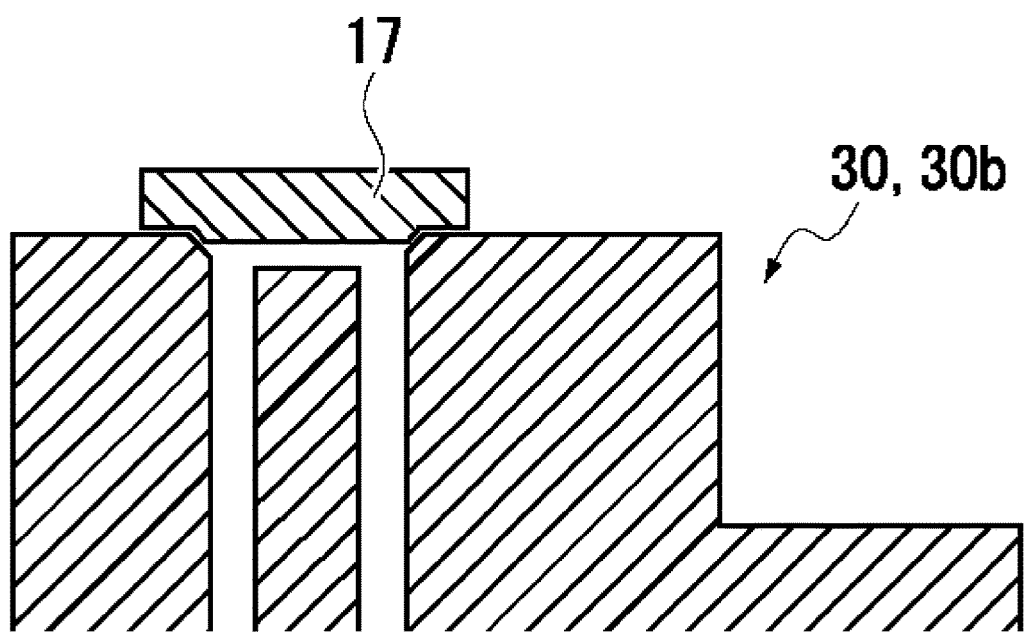
FIG. 22 is an explanatory diagram of another technology adoptable for improving the hermetic closing property of the sensor cartridge.

In order to seal the sensor cartridges 30, 30b further preferably, as schematically illustrated in FIG. 22, the sealing rubber 17 may involve adopting a sealing rubber taking such a shape as to fit to the port portion of each of the sensor cartridges 30, 30b, and the sealing member 152 may also involve adopting a sealing member taking such a shape as to fit to the aperture of the sensor cartridge 130. When the fitting portion has an excessively large length, however, the sliders 15, 150 become hard to slide. Therefore, when adopting the sealing rubber 17/sealing member 152 taking the shapes described above, it is preferable that the length of the fitting portion is set not to become excessively large.

The measurement apparatus according to each of the embodiments may be modified into an apparatus configured so that the tip of each of the sliders 15, 150 does not protrude from the enclosure 10. Each of the sliders 15, 150 may be modified into a slider to hold the sensor by a portion other than the tip thereof. The measurement apparatus according to each of the embodiments may be modified into an apparatus configured so that the second position is unrelated to the sealing of the sensor cartridge (e.g., an apparatus configured so that the sensor cartridge is sealed when the slider is located in the first position and a position between the first position and the second position). The measurement apparatus according to each of the embodiments may be modified into an apparatus configured to hermetically close the sensor cartridge also when making the measurement (applying the droplet) by increasing the length of each of the sealing rubber 17 and the sealing member 152 of the measurement apparatuses according to the respective embodiments. Some functions may also be removed from the respective measurement apparatuses/sensor cartridges described above. It is also a matter of course that the respective measurement apparatuses/sensor cartridges may be modified into measurement apparatuses/sensor cartridges for measuring some sort of physical quantities related to not the blood but other measurement targets.

What is claimed is:

1. A measurement apparatus to measure a physical quantity related to a measurement target by use of a sensor, comprising:
    an apparatus enclosure;
    a controller electrically connected to the sensor; and
    a moving member disposed inside the apparatus enclosure and including a sensor holder that holds the sensor,
    the moving member being movable to protrude the sensor holder outwardly of the apparatus enclosure such that the sensor is spaced away from the entire apparatus enclosure, and further including a conductor to electrically connect the sensor to the controller.

2. The measurement apparatus according to claim 1, further comprising a flexible board to electrically connect the conductor to the controller.

3. The measurement apparatus according to claim 1, wherein the moving member is molded integrally with the conductor.

4. The measurement apparatus according to claim 1, wherein the sensor holder is housed in the apparatus enclosure when standing by.

5. The measurement apparatus according to any one of claim 1, wherein the moving member includes a main slider and a sub-slider, and
    the sensor is pinched in between the main slider and the sub-slider and is thus held.

6. The measurement apparatus according to claim 1, further comprising a housing that houses a sensor cartridge containing a plurality of built-in sensors,
    the moving member including a hermetic closure to seal an aperture of the sensor cartridge when standing by and moving to protrude the sensor outwardly of the apparatus enclosure.

7. The measurement apparatus according to claim 1, wherein the apparatus enclosure houses the sensor to which a droplet of measurement target having a physical quantity is applied, and
    the moving member advances and retreats between a first position with the sensor protruding from the apparatus enclosure, a second position with the sensor retreating from the first position, and a third position with the sensor appearing in a position to engage with the moving member advancing to the first position by retreating from the second position.

8. The measurement apparatus according to claim 7, wherein the moving member causes the sensor to appear in front of the tip of the moving member by retreating to the third position from the second position, and the tip of the moving member holds the sensor appearing in front thereof when advancing to the first position from the third position.

9. The measurement apparatus according to claim 8, further comprising a carrying mechanism to carry the sensor to the front of the tip in the third position in linkage with the retreat of the moving member to the third position.

10. The measurement apparatus according to claim 7, further comprising: a sensor housing to be provided within the apparatus enclosure and to have an outlet of the sensor; and
    an opening/closing member to close the outlet when the moving member is located at least in the second position and to open the outlet when the moving member is located at least in the third position.

11. The measurement apparatus according to claim 7, wherein the apparatus enclosure is provided with a protrude portion to keep the position of the moving member in the first position and a protruded portion to keep the position of the moving member in the second position, and
    the moving member includes an engaging portion to cause the moving member to engage with the apparatus enclosure in the first position or the second position by engaging with the protruded portion of the apparatus enclosure, the engaging portion becoming flexural upon applying force onto the moving member in the retreating direction and thereby moving over the protruded portion kept in engagement.

12. The measurement apparatus according to claim 7, further comprising a disengaging mechanism to disengage the sensor from the moving member when the moving member retreats to the second position from the first position.

13. The measurement apparatus according claim 12, wherein the disengaging mechanism includes a movement inhibiting member to inhibit the sensor from moving together with the moving member by abutting on an edge, on the side of the moving member, of the sensor held by the moving member being on the movement toward the second position.

14. The measurement apparatus according to claim 7, wherein the moving member includes:
    a first slider to move the sensor being movable between the first position and the third position to such a position as to abut on a tip of the first slider when moving to the third position from the second position, the sensor having moved to the abutting position engaging with the tip of the first slider when moving to the first position; and
    a second slider to pinch the sensor between a tip of the second slider and the tip of the first slider by fitting to the first slider after the sensor has engaged with the tip of the first slider being on the movement toward the first position.

15. The measurement apparatus according to claim 7, wherein the sensor is a sensor housed in the sensor cartridge set in the apparatus enclosure,
    the sensor cartridge including:
    a reel to be wound with a sensor element having a plurality of sensors bonded one by one onto one surface of a tape-shaped mount film along a longitudinal direction of the mount film, the sensor having an end portion being exfoliated from the mount film when bending a portion with existence of the end portion of a certain sensor at a curvature equal to or smaller than a predetermined curvature in the longitudinal direction so that one surface side of the sensor is convexed;
    a case to have a sensor protrusion port and to house the reel therein, the sensor element being disposed in the case so that the sensor element unwound from the reel passes through the sensor protrusion port and is bent toward the film housing port to exfoliate a part of the sensor from the mount film of the sensor element; and a rotary body to be housed in the case and enabled to rotate from outside the case, the rotary body moving the sensor element within the case in an unwinding direction of the sensor element wound on the reel by the rotary body rotating in a predetermined direction from outside the case, the measurement apparatus further comprising a drive mechanism to rotate the rotary body of the sensor cartridge housed in the housing in the predetermined direction so that a next sensor protrudes from the sensor protrusion port of the case by converting a part of rectilinear motion of the moving member toward the third position into a rotary motion.

16. A method for operating a measurement apparatus comprising an apparatus enclosure to house a sensor to which a droplet of measurement target having a physical quantity is applied; and a moving member to protrude the sensor from the apparatus enclosure in a state of holding the sensor such that the sensor is spaced away from the entire apparatus enclosure, the method comprising:

causing the sensor to appear in such a position that the moving member, disposed inside the apparatus enclosure, engages with the sensor by retreating the moving member to a third position from a second position as a standby position;

protruding the sensor from the apparatus enclosure by advancing the moving member to a first position in front of the second position from the third position to engage with the sensor; and retreating the moving member to the second position from the first position after applying the droplet of measurement target to the sensor protruded from the apparatus enclosure.

17. The method for operating the measurement apparatus according to claim 16, wherein the causing the sensor to appear includes causing the sensor to appear in front of a tip of the moving member, and the protruding the sensor includes causing the tip of the moving member to engage with the sensor appearing in front of the tip thereof.

* * * * *